US011592366B2

(12) United States Patent
Bomsztyk et al.

(10) Patent No.: US 11,592,366 B2
(45) Date of Patent: Feb. 28, 2023

(54) ULTRASOUND SYSTEM FOR SHEARING CELLULAR MATERIAL IN A MICROPLATE

(71) Applicant: Matchstick Technologies, Inc., Kirkland, WA (US)

(72) Inventors: Karol Bomsztyk, Mercer Island, WA (US); Greg P. Darlington, Snohomish, WA (US); Brian E. MacConaghy, Seattle, WA (US); Thomas J. Matula, Kirkland, WA (US); Adam D. Maxwell, Lynwood, WA (US)

(73) Assignees: Matchstick Technologies, Inc., Kirkland, WA (US); University of Washington, Seattle, WA (US)

( * ) Notice: Subject to any disclaimer, the term of this patent is extended or adjusted under 35 U.S.C. 154(b) by 263 days.

(21) Appl. No.: 16/801,087

(22) Filed: Feb. 25, 2020

(65) Prior Publication Data
US 2020/0209115 A1    Jul. 2, 2020

Related U.S. Application Data

(62) Division of application No. 15/873,857, filed on Jan. 17, 2018, now Pat. No. 10,809,166.
(Continued)

(51) Int. Cl.
*H01L 41/187* (2006.01)
*G01N 1/28* (2006.01)
(Continued)

(52) U.S. Cl.
CPC ........... *G01N 1/286* (2013.01); *B06B 1/0215* (2013.01); *B06B 1/0622* (2013.01);
(Continued)

(58) Field of Classification Search
CPC ... B06B 1/0215; B06B 1/0622; B06B 1/0629; H01L 41/04
See application file for complete search history.

(56) References Cited

U.S. PATENT DOCUMENTS

| | | |
|---|---|---|
| 3,949,349 A | 4/1976 | Massa et al. |
| 5,858,309 A | 1/1999 | Mathus et al. |
| (Continued) | | |

FOREIGN PATENT DOCUMENTS

| | | |
|---|---|---|
| WO | 2006014140 A1 | 2/2006 |
| WO | 2010118540 A1 | 10/2010 |
| WO | 2016011075 A1 | 1/2016 |

OTHER PUBLICATIONS

Matula et al., "MTLS 971: Sonochemical sample preparation for biological assays—A potential tool for sample processing," presentation at PacifiChem conference, Dec. 15-20, 2015, Honolulu, Hawaii, USA.

*Primary Examiner* — Bryan P Gordon
(74) *Attorney, Agent, or Firm* — Clements Bernard Walker

(57) ABSTRACT

Disclosed embodiments include illustrative piezoelectric element array assemblies, methods of fabricating a piezoelectric element array assembly, and systems and methods for shearing cellular material. Given by way of non-limiting example, an illustrative piezoelectric element array assembly includes at least one piezoelectric element configured to produce ultrasound energy responsive to amplified driving pulses. A lens layer is bonded to the at least one piezoelectric element. The lens layer has a plurality of lenses formed therein that are configured to focus ultrasound energy created by single ones of the at least one piezoelectric element into a plurality of wells of a microplate disposable in ultrasonic communication with the lens layer, wherein more
(Continued)

than one of the plurality of lenses overlie single ones of the at least one piezoelectric element.

10 Claims, 17 Drawing Sheets

Related U.S. Application Data

(60) Provisional application No. 62/448,857, filed on Jan. 20, 2017.

(51) Int. Cl.

| | | |
|---|---|---|
| *C12Q 1/6806* | (2018.01) | |
| *B06B 1/06* | (2006.01) | |
| *H01L 41/04* | (2006.01) | |
| *B06B 1/02* | (2006.01) | |
| *C12N 13/00* | (2006.01) | |
| *G10K 11/30* | (2006.01) | |
| *C12M 1/00* | (2006.01) | |
| *H01L 41/25* | (2013.01) | |
| *G01N 1/40* | (2006.01) | |

(52) U.S. Cl.
CPC .......... *B06B 1/0629* (2013.01); *C12M 47/06* (2013.01); *C12N 13/00* (2013.01); *C12Q 1/6806* (2013.01); *G10K 11/30* (2013.01); *H01L 41/04* (2013.01); *H01L 41/1876* (2013.01); *B06B 2201/55* (2013.01); *B06B 2201/70* (2013.01); *G01N 2001/2873* (2013.01); *G01N 2001/4094* (2013.01); *H01L 41/25* (2013.01)

(56) References Cited

U.S. PATENT DOCUMENTS

| | | | |
|---|---|---|---|
| 6,436,351 | B1 | 8/2002 | Gubernator et al. |
| 6,699,711 | B1 | 3/2004 | Hahn et al. |
| 6,719,449 | B1 | 4/2004 | Laugham et al. |
| 7,687,026 | B2 | 10/2010 | Laugham et al. |
| 7,951,337 | B2 | 5/2011 | Vollert |
| 8,127,614 | B2 | 3/2012 | Vivek et al. |
| 8,319,398 | B2 | 11/2012 | Vivek et al. |
| 2002/0141905 | A1 | 10/2002 | Sha et al. |
| 2009/0233814 | A1 | 9/2009 | Bashkirov et al. |
| 2010/0028988 | A1 | 2/2010 | Chu et al. |
| 2010/0289887 | A1 | 11/2010 | Charlot et al. |
| 2015/0343493 | A1* | 12/2015 | Hajati ............... B06B 1/0215 367/87 |
| 2016/0178500 | A1* | 6/2016 | Totoki ............. G01N 15/0227 356/338 |
| 2017/0205318 | A1* | 7/2017 | Matula ............... B01L 3/5085 |
| 2018/0209878 | A1* | 7/2018 | Matula ................ C12M 47/06 |
| 2018/0374471 | A1* | 12/2018 | Dirksen ............. B06B 1/0292 |

\* cited by examiner

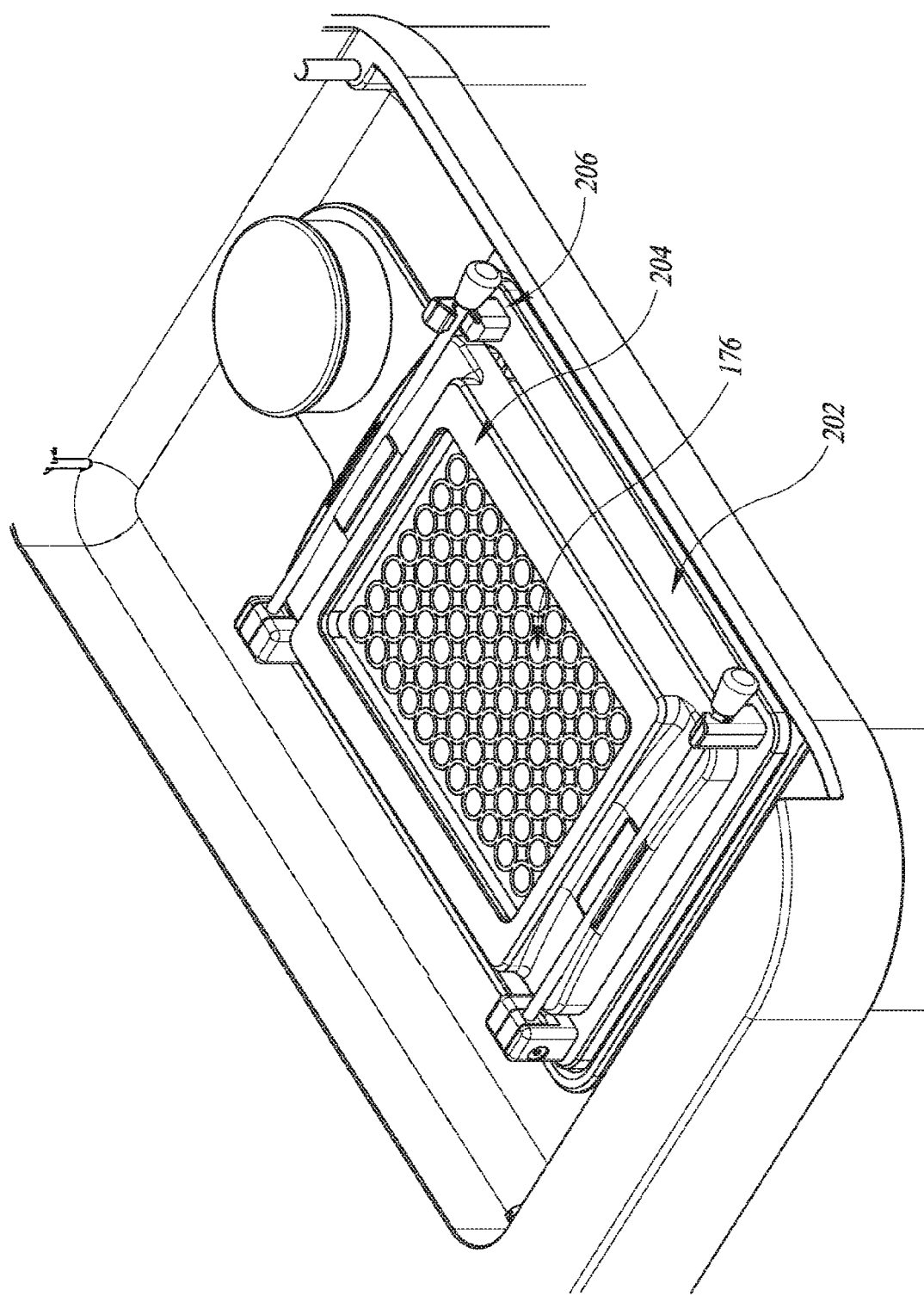

ULTRASOUND SYSTEM FOR SHEARING CELLULAR MATERIAL IN A MICROPLATE

CROSS-REFERENCE TO RELATED APPLICATIONS

The present application is related to, and claims the benefit of priority of the filing date of, U.S. Provisional Patent Application No. 62/448,857 filed Jan. 20, 2017, which is herein incorporated by reference in its entirety. The present application also relates to improvements to subject matter disclosed in PCT Application No. PCT/US2015/040444 filed Jul. 14, 2015, which is herein incorporated by reference in its entirety.

STATEMENT REGARDING FEDERALLY SPONSORED RESEARCH

Disclosed subject matter was made with government support under grant nos. 1 R21 GM 111439-01 and 1 R33 CA 191135-01 awarded by the National Institutes of Health. The government has certain rights in the disclosed subject matter.

FIELD

The present disclosure is related to ultrasound systems for shearing cellular material.

BACKGROUND

The statements in this section merely provide background information related to the present disclosure and may not constitute prior art.

Sample preparation is one of the preliminary steps that is performed before biological samples are analyzed. Sample preparation often involves the breakdown of the material into cellular or subcellular fragments. One particular application is the breaking up (or shearing) of DNA or Chromatin into smaller fragments. Ultrasound is one known method of breaking down material. In some prior art devices, biological samples are placed into a test tube that is put into a liquid bath and subjected to high intensity ultrasound waves—similar to a jewelry cleaner, but with much higher power levels. To avoid an uneven exposure of the sample, the test tube is moved around within the variable ultrasound field as it is processed. While this approach does work, it is limited to processing a single (or a few) test tube sample(s) at a time, thereby resulting in long processing times. Moreover, non-uniform ultrasound fields may create hot and cold spots that require that the test tube be moved around to get consistent shearing.

To increase the throughput of cellular processing, some currently known systems analyze cellular samples in microplates. As will be appreciated by those skilled in the art, a microplate is a tray that contains an array of wells in which samples can be placed for analysis. Advantages of using microplates include processing such trays with automated equipment and processing multiple samples at the same time without moving the samples from one vessel to another.

One currently known system for shearing cellular samples in a microplate uses ultrasonically vibrating pins that extend into the wells. However, this can lead to cross contamination between the various wells and requires extensive cleaning of the pins. It is also not very useful for tissue samples. Furthermore, the quality of the results depends greatly on the exact position of the tips in the sample.

Another currently known approach uses a large ultrasound transducer that is positioned below a single well and focuses the energy within the well. The focused ultrasound energy creates cavitation in the sample material that is in the well but only one well is processed at a time. For a 96 element microplate, the processing time to shear all the samples can exceed several hours during which some samples may degrade.

Another currently known approach uses a device that processes a column or row of 8 or 12 DNA samples—but it cannot process chromatin. This device is a subset of 96 wells—not the entire microplate.

Another currently known approach to processing cellular material in a microplate is to place a single ultrasound transducer below each well. See, for example, U.S. Pat. No. 6,699,711 to Hahn et al. ("Hahn"). However, when trying to experiment with the system described in the Hahn patent for use in analyzing biological materials including DNA and chromatin, it was found that the system was ineffective in shearing chromatin without causing the transducers to break.

Another currently known approach uses a large ultrasonic horn in which the entire microplate is processed at once. However, the wells are not processed evenly because the system operates at low kHz frequencies and there are hot/cold spots that result in uneven processing.

SUMMARY

Disclosed embodiments include illustrative piezoelectric element array assemblies, methods of fabricating a piezoelectric element array assembly, and systems and methods for shearing cellular material.

In an embodiment, an illustrative piezoelectric element array assembly is provided. The piezoelectric element array assembly includes at least one piezoelectric element configured to produce ultrasound energy responsive to amplified driving pulses. A lens layer is bonded to the at least one piezoelectric element. The lens layer has a plurality of lenses formed therein that are configured to focus ultrasound energy created by single ones of the at least one piezoelectric element into a plurality of wells of a microplate disposable in ultrasonic communication with the lens layer, wherein more than one of the plurality of lenses overlie single ones of the at least one piezoelectric element.

In another embodiment, an illustrative method of fabricating a piezoelectric element array assembly is provided. The method includes: providing at least one piezoelectric element configured to produce ultrasound energy responsive to amplified driving pulses; and bonding a lens layer to the at least one piezoelectric element, the lens layer having a plurality of lenses formed therein that are configured to focus ultrasound energy created by single ones of the at least one piezoelectric element into a plurality of wells of a microplate disposable in ultrasonic communication with the lens layer, wherein more than one of the plurality of lenses overlie single ones of the at least one piezoelectric element.

In another embodiment, an illustrative system for shearing cellular material is provided. The system includes a signal generator configured to generate ultrasound driving pulses. An amplifier is electrically coupled to the signal generator and configured to amplify the ultrasound driving pulses. A piezoelectric element array includes at least one piezoelectric element configured to produce ultrasound energy responsive to amplified driving pulses; and a plurality of lenses, wherein more than one of the plurality of lenses overlie single ones of the at least one piezoelectric element and wherein single ones of the plurality of lenses are configured to focus ultrasound energy into single ones of a plurality of wells of a microplate.

In another embodiment, an illustrative method includes: generating ultrasound driving pulses; amplifying the ultrasound driving pulses; producing ultrasound energy with at least one piezoelectric element responsive to the amplified driving pulses; and focusing the ultrasound energy created by single ones of the at least one piezoelectric element into a plurality of wells of a microplate by a plurality of lenses, wherein more than one of the plurality of lenses overlie single ones of the at least one piezoelectric element and wherein single ones of the plurality of lenses are ultrasonically coupled to single ones of the plurality of wells.

In another embodiment, another illustrative system for shearing cellular material is provided. The system includes a computer processor configured to generate timing signals. A signal generator is configured to generate ultrasound driving pulses responsive to the timing signals. An amplifier is electrically coupled to the signal generator and is configured to amplify the ultrasound driving pulses. A plurality of piezoelectric elements is arranged in an array of rows and columns. The piezoelectric elements are configured to produce ultrasound energy responsive to amplified driving pulses. The timing signals are generated such that adjacent ones of the plurality of piezoelectric elements are not energized by at least amplified driving pulses chosen from simultaneous driving pulses and temporally sequential driving pulses. More than one of a plurality of lenses overlie single ones of the plurality of piezoelectric elements and single ones of the plurality of lenses are configured to focus ultrasound energy into single ones of a plurality of wells of a microplate.

In another embodiment, another illustrative system for shearing cellular material is provided. The system includes a housing. A signal generator is disposed in the housing and is configured to generate ultrasound driving pulses. An amplifier is disposed in the housing and is electrically coupled to the signal generator, and the amplifier is configured to amplify the ultrasound driving pulses. A piezoelectric element array is disposed in the housing. The piezoelectric element array includes at least one piezoelectric element configured to produce ultrasound energy responsive to amplified driving pulses. A plurality of lenses are configured to focus ultrasound energy into a plurality of wells of a microplate. A fluidics system is configured to flow therein a transducer fluid. A seal is disposed on the housing. The seal is configured to receive a microplate in sealing engagement thereon such that the piezoelectric element array, the housing, and a microplate received in sealing engagement on the seal define a chamber in hydraulic communication with the fluidics system and configured to contain therein transducer fluid.

In an another embodiment, an illustrative method of shearing cellular material is provided. The method includes: placing a microplate with cellular material disposed in a plurality of wells defined therein on a seal disposed on a housing; clamping the microplate on the seal in sealing engagement therewith; flowing transducer fluid in a fluidics system disposed in the housing such that transducer fluid is placed in hydraulic communication with a plurality of lenses; energizing an array of piezoelectric elements to produce ultrasound energy; and focusing ultrasound energy in the plurality of wells with a plurality of lenses such that cavitation is induced in the cellular material disposed in the plurality of wells.

Further features, advantages, and areas of applicability will become apparent from the description provided herein.

It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIGS. 7B-7D are perspective views in partial cutaway of details of the system of FIG. 7A.

DETAILED DESCRIPTION

The following description is merely illustrative in nature and is not intended to limit the present disclosure, application, or uses.

As will be discussed in further detail below, disclosed embodiments include illustrative piezoelectric element array assemblies, methods of fabricating a piezoelectric element array assembly, and systems and methods for shearing cellular material. Given by way of overview, in various embodiments a sufficient amount of ultrasound energy is applied simultaneously to a number of samples in order to cause inertial cavitation to occur in the samples, thereby causing some shearing of molecular bonds of DNA and chromatin in the samples.

As discussed above, one of the difficulties of using ultrasound to shear the cellular material is that some currently known transducer elements can crack when driven to a level that is sufficient to cause cavitation. Various embodiments of subject matter disclosed herein relate to improvements to transducer design that improve the durability of the transducer elements.

Still by way of overview, various embodiments of subject matter disclosed herein relate to illustrative piezoelectric element array assemblies that can focus ultrasound energy from a single piezoelectric element to more than one well of a microplate and to illustrative methods for fabrication of such piezoelectric element array assemblies. Various embodiments of subject matter disclosed herein also relate to systems and methods for shearing cellular material in which such piezoelectric element array assemblies may be employed. Various embodiments of subject matter disclosed herein also relate to systems and methods for shearing cellular material in which improvements have been made to currently known aspects related to ultrasonically coupling piezoelectric element arrays to microplates with transducer fluid.

Now that an overview has been provided, details will be set forth below by way of non-limiting examples and not of limitation.

Figure 1A:
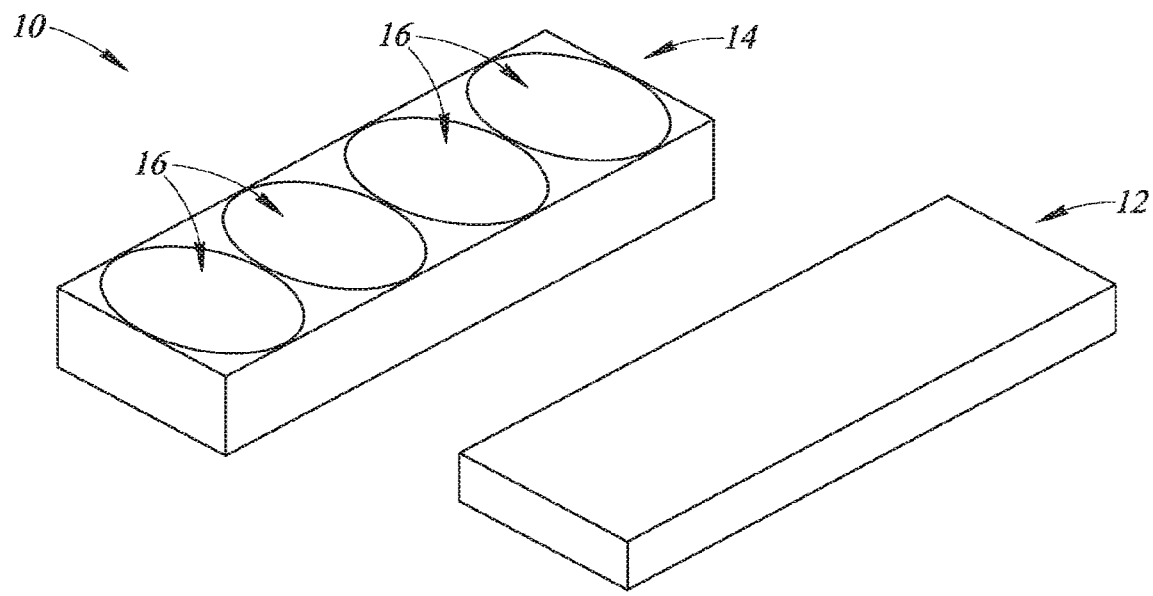
FIG. 1A is an exploded perspective view of an illustrative piezoelectric element array assembly.

Referring now to FIG. 1A, an illustrative piezoelectric element array assembly 10 can focus ultrasound energy from a single piezoelectric element 12 to more than one well of a microplate (not shown). In various embodiments, the piezoelectric element array assembly 10 includes at least one piezoelectric element 12 configured to produce ultrasound energy responsive to amplified driving pulses. A lens layer 14 is bonded to the piezoelectric element 12. The lens layer 14 has lenses 16 formed therein. Each lens 16 is configured to focus ultrasound energy into one well of a microplate (not shown in FIG. 1A) that is disposed in ultrasonic communication with the lens layer 12. As shown in FIG. 1A, more than one lens 16 overlies the single piezoelectric element 12. As such, the piezoelectric element array assembly 10 can focus ultrasound energy from a single piezoelectric element 12 to more than one well of a microplate (not shown in FIG. 1A)—because more than one lens 16 overlies the single piezoelectric element 12.

Still referring to FIG. 1A, in various embodiments the piezoelectric element 12 may include a strip of piezoelectric substrate material such as lead zirconate titanate (Pb[Zr(x) Ti(1−x)]O3) ("PZT") that is coated or plated on both sides with a conductor such as aluminum, gold, copper, or the like. The piezoelectric element 12 has width, length, and thickness dimensions that are selected to prevent cracking when driven with a voltage signal that is sufficient to cause cavitation in a well of a microplate.

In various embodiments each piezoelectric element 12 may have a width equal to the width of a single well of a microplate and a length selected to underlie more than one well of a microplate. Accordingly, it will be appreciated that more than one lens 16 may overlie any single piezoelectric element 12. Thus, the piezoelectric element array assembly 10 can focus ultrasound energy from a single piezoelectric element 12 to more than one well of a microplate (not shown in FIG. 1A) because more than one lens 16 overlies the single piezoelectric element 12.

As discussed above, in some embodiments each piezoelectric element 12 may have a length selected to underlie more than one well of a microplate. In some embodiments and as shown in FIG. 1A, the piezoelectric element 12 may have a length selected to underlie four wells of a microplate and a width equal to the width of a single well. As such, four of the lenses 16 overlie the single piezoelectric element 12. Using conventional microplate dimensions, the length and width of the piezoelectric element 12 as shown in FIG. 1A is approximately 36×9 mm.

In various embodiments the lens layer 14 has concave lenses 16 formed in an upper surface thereof. The lenses 16 operate to focus the ultrasonic plane waves created by the piezoelectric element 12 as the piezoelectric element 12 is excited by a driving voltage. The lenses 16 are shaped to focus the plane waves into a well of a microplate (not shown) that is positioned above the lens layer 14.

Figure 1B:
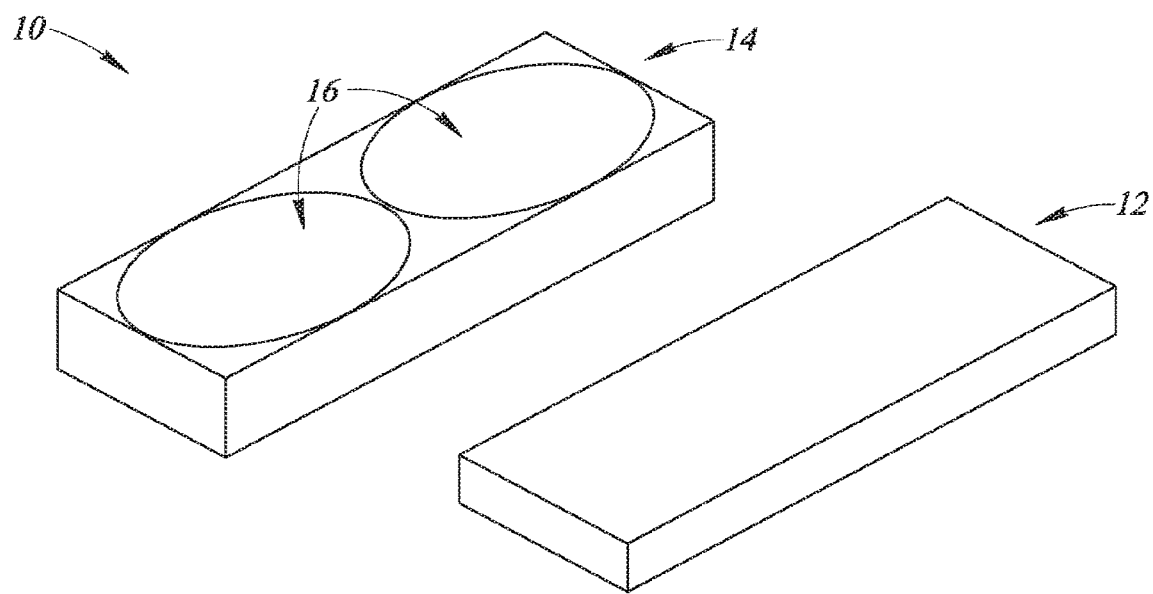
FIG. 1B is an exploded perspective view of another illustrative piezoelectric element array assembly.
Figure 1C:
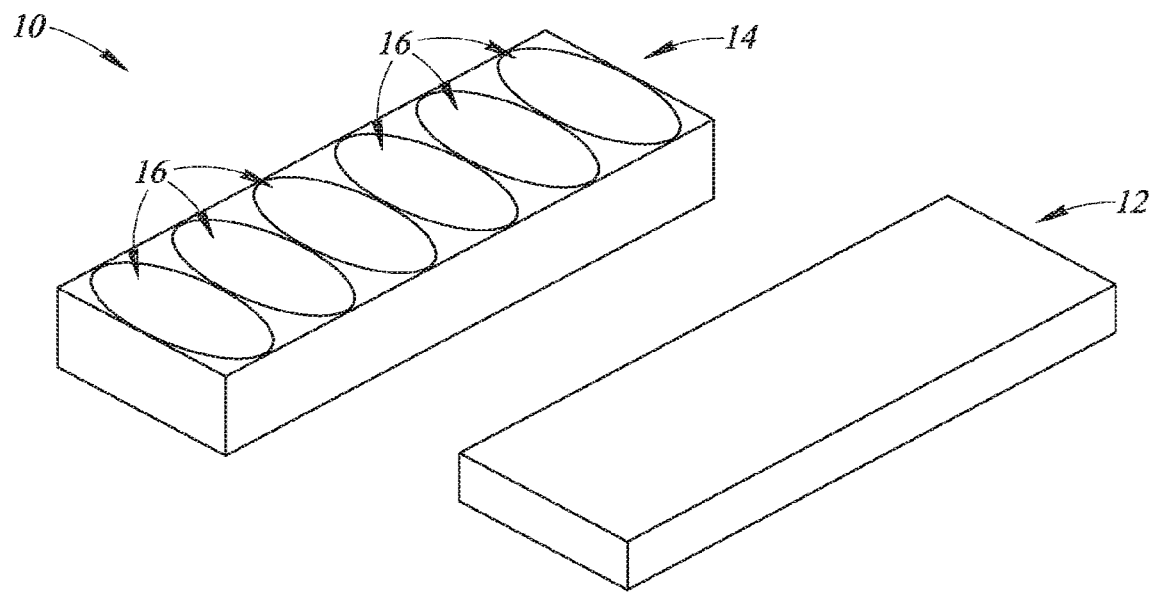
FIG. 1C is an exploded perspective view of another illustrative piezoelectric element array assembly.
Figure 1D:
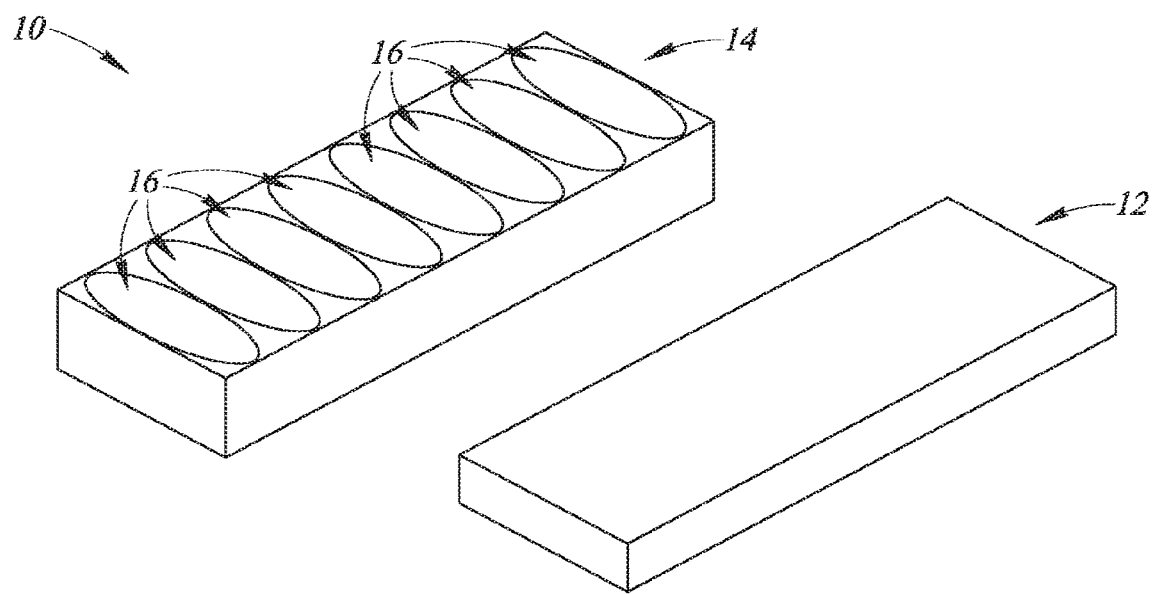
FIG. 1D is an exploded perspective view of another illustrative piezoelectric element array assembly.
Figure 1E:
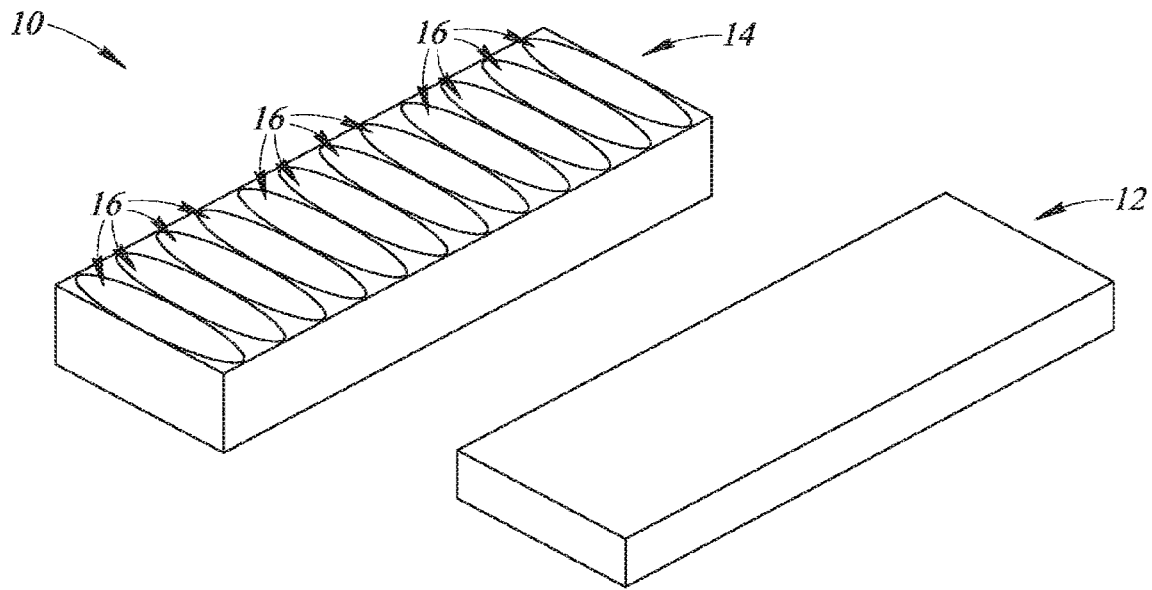
FIG. 1E is an exploded perspective view of another illustrative piezoelectric element array assembly.

It will be appreciated that in other embodiments piezoelectric elements 12 of other sizes could be used and any number of lenses 16 may overlie the piezoelectric element 12 as desired for a particular application. For example and referring to FIG. 1B, in some embodiments the piezoelectric element 12 may have a length selected to underlie two wells of a microplate and a width equal to the width of a single well. As such, two of the lenses 16 overlie the single piezoelectric element 12. As another example and referring to FIG. 1C, in some embodiments the piezoelectric element 12 may have a length selected to underlie six wells of a microplate and a width equal to the width of a single well. As such, six of the lenses 16 overlie the single piezoelectric element 12. As another example and referring to FIG. 1D, in some embodiments the piezoelectric element 12 may have a length selected to underlie eight wells of a microplate and a width equal to the width of a single well. As such, eight of the lenses 16 overlie the single piezoelectric element 12. As another example and referring to FIG. 1E, in some embodiments the piezoelectric element 12 may have a length selected to underlie twelve wells of a microplate and a width equal to the width of a single well. As such, twelve of the lenses 16 overlie the single piezoelectric element 12. However, no limitation other to the number of lenses 16 which may overlie the single piezoelectric element 12 is intended and is not to be inferred—other than more than one lens 16 overlies the single piezoelectric element 12. Moreover, no limitation is intended to the width of the piezoelectric elements 12, which may have any width as desired for a particular application, such as arrays of 2×2, 2×4, 3×4, and the like.

It will be appreciated that, in each embodiment, the piezoelectric element 12 is sized to deliver ultrasound energy to two or more wells in the microplate so that the stresses created in the strip are spread out over an area that is larger than the area of a single well. In one embodiment, the thickness of the piezoelectric element 12 is selected to produce ultrasound energy at a frequency selected between 500 KHz and 2 MHz.

Figure 1F:
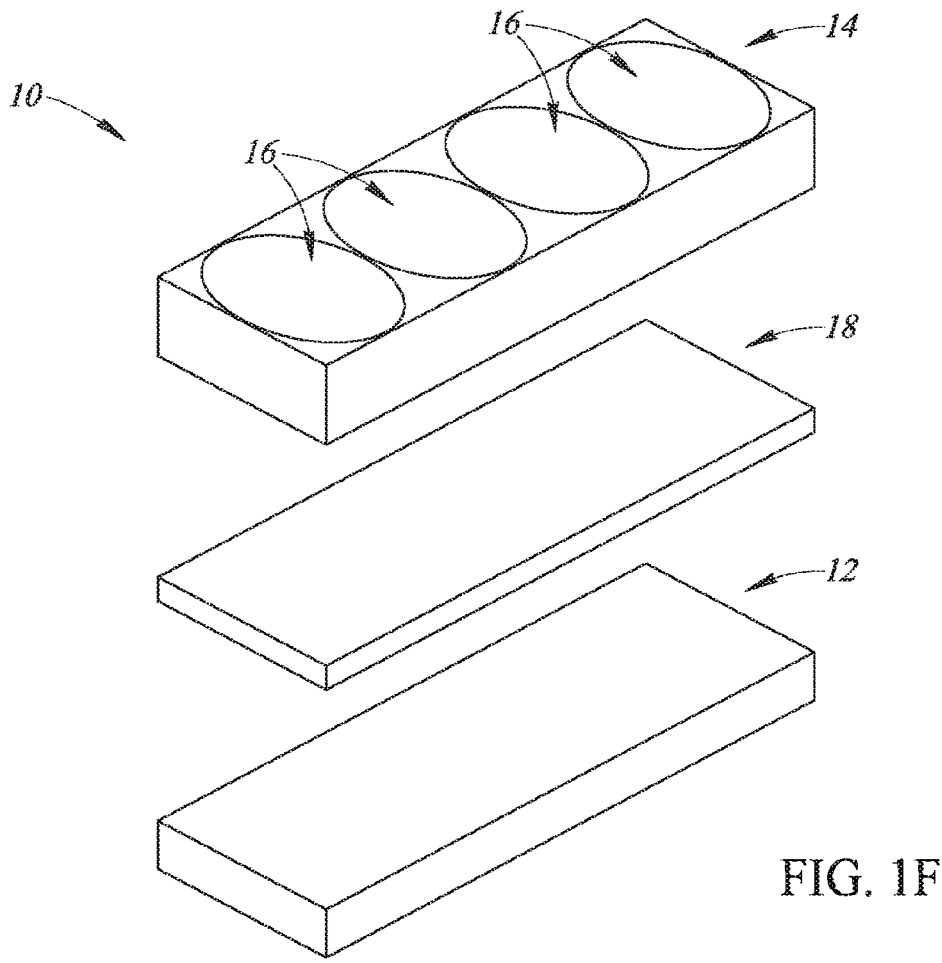
FIG. 1F is an exploded perspective view of another illustrative piezoelectric element array assembly.

Referring now to FIG. 1F and depending on the impedance of the lens layer 14, in some embodiments an optional matching layer 18 may be positioned between the piezoelectric element 12 and the lens layer 14. In various embodiments the matching layer 18 has a thickness of ¼ wavelength at the operating frequency of the system and is bonded to the upper surface of the piezoelectric element 12 and the bottom of the lens layer 14 with an adhesive, such as without limitation epoxy. It will be appreciated that the optional matching layer 18 may be used in conjunction with piezoelectric elements 12 of any size, such as those discussed above.

In various embodiments, the matching layer 18 may be omitted. For example, in some embodiments the lens layer 14 is made of a material having an acoustic impedance that is between the impedance of the piezoelectric element 12 and a coupling fluid (not shown), such as without limitation water or gel, that is placed in ultrasonic communication between the lens layer 14 and the wells of a microplate. In such embodiments, the matching layer 18 suitably is omitted. In some embodiments the lens layer 14 may be made of a suitable material such as graphite, fluorphlogopite mica in a borosilicate glass matrix, and the like.

Figure 2A:
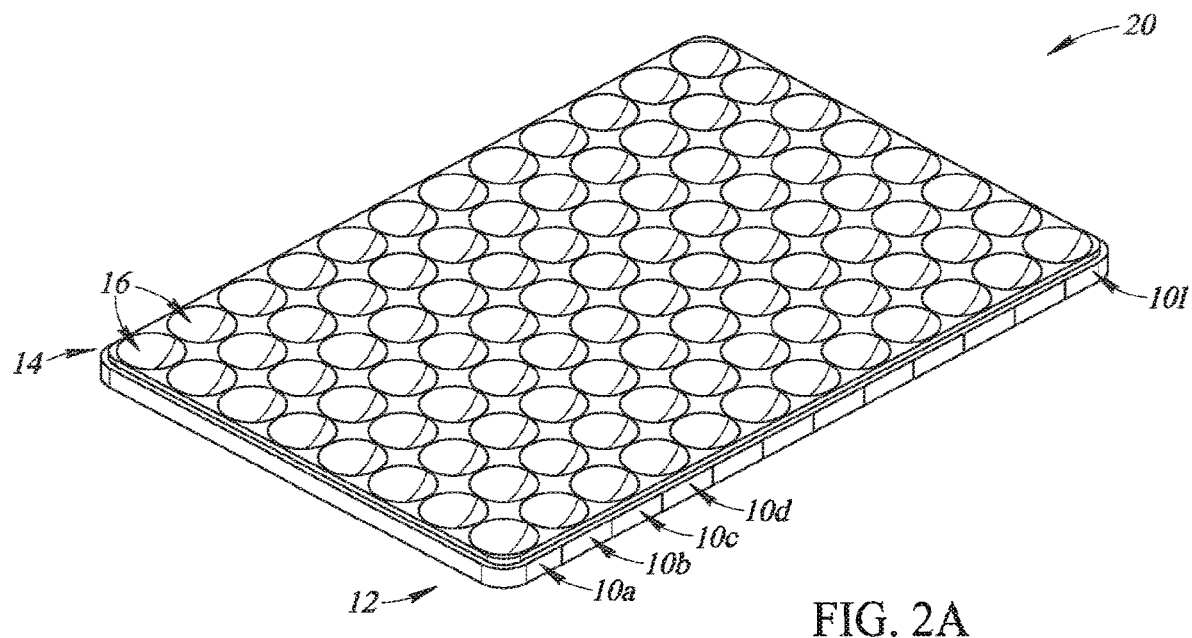
FIG. 2A is a perspective view of an illustrative array of piezoelectric element array assemblies.
Figure 2B:
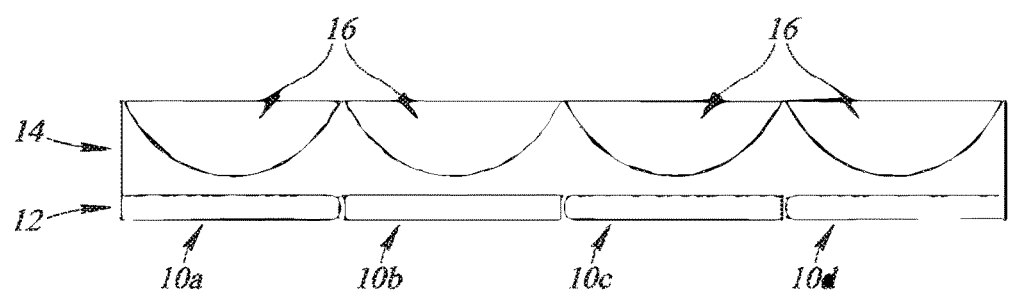
FIG. 2B is a side plan view in partial cutaway of a portion of the array of piezoelectric element array assemblies of FIG. 2A.
Figure 2C:
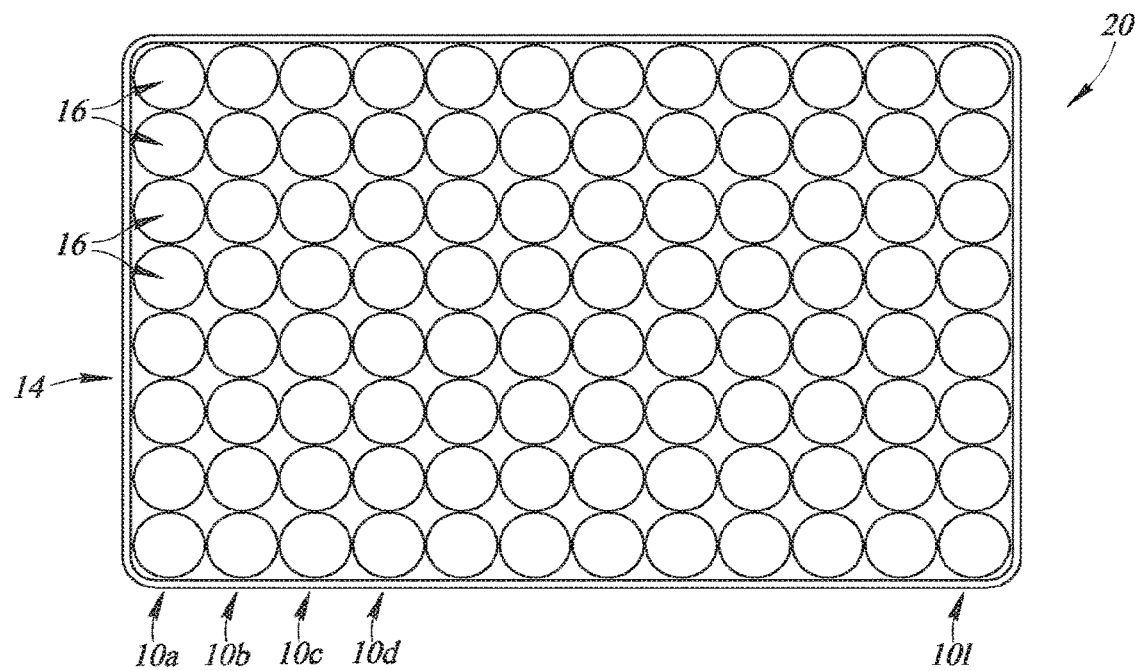
FIG. 2C is a top plan view of the array of piezoelectric element array assemblies of FIG. 2A.

Referring now to FIGS. 2A-2C, embodiments of piezoelectric element array assemblies 10a, 10b, 10c, 10d . . . 10l are arranged in an array 20 of rows and columns to deliver ultrasound energy to all the wells of a ninety-six (96) well microplate (not shown). It will be appreciated that in various embodiments a larger or smaller number of piezoelectric element array assemblies 10 could be used to accommodate different sized microplates. It will also be appreciated that, while the piezoelectric element array assemblies 10a, 10b, 10c . . . 10l are shown as being sized such that four (4) lenses 16 overlie each piezoelectric element array assembly 10, in various embodiments the piezoelectric element array assemblies 10 may be sized as desired such that two or more lenses 16 overlie each piezoelectric element array assembly 10 (as shown in FIGS. 1A-1E). In various embodiments the piezoelectric element array assemblies 10 are preferably held in a frame (not shown) that maintains the arrangement of the piezoelectric element array assemblies 10 below the microplate (not shown). In some embodiments, the size of the piezoelectric elements 12 may be slightly larger than the size of the lens layer 14 in order to allow a wrap-around electrode (not shown) to be used to connect electrical wires to the piezoelectric elements 12.

Figure 3:
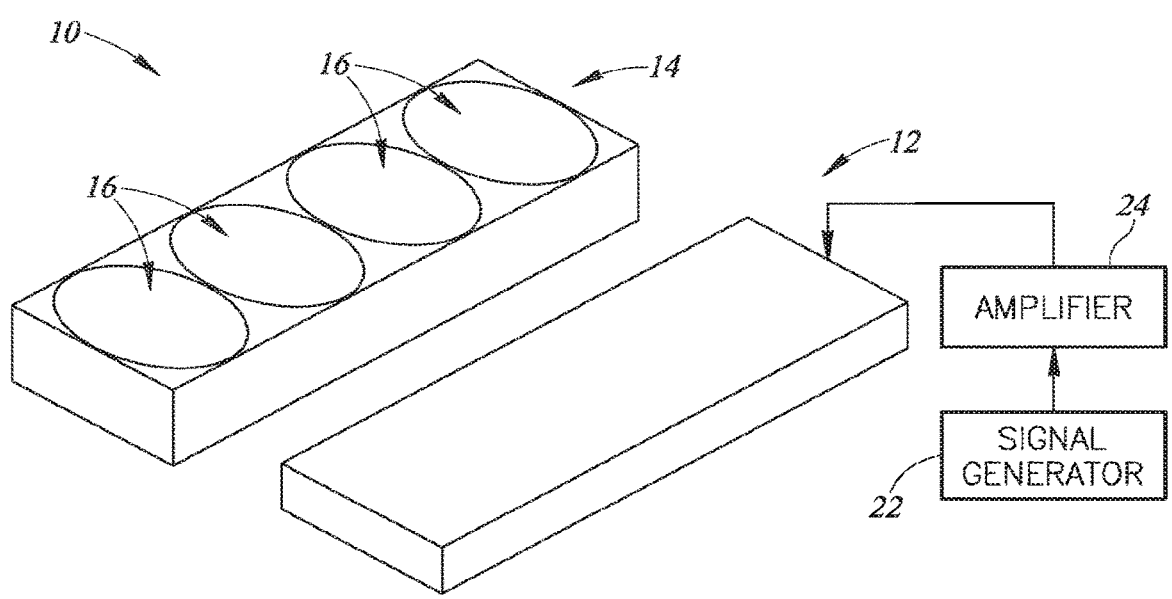
FIG. 3 is an exploded perspective view in partial schematic form of an illustrative system for shearing cellular material.

Referring to FIG. 3, in various embodiments and as an introduction to illustrative system environments in which cellular material is sheared with ultrasound energy, a signal generator 22 produces driving signals that are amplified by an amplifier 24 and each piezoelectric element 12 is electrically connected to the amplifier 24. In various embodiments, the driving signals may be waveforms such as short bursts of pulses (such as without limitation 10-50 microseconds or so) that are amplified to a sufficient voltage level (such as approximately 400 V) so that the acoustic energy produced is sufficient to cause inertial cavitation in the cellular material in a well. In some embodiments, the bursts are spaced in time to reduce heating the sample and the coupling fluid.

In some embodiments each piezoelectric element 12 may be electrically connected to the amplifier 24 individually. In some other embodiments piezoelectric elements 12 may be electrically connected in parallel. In some such embodiments, adjacent piezoelectric elements 12 may be electrically connected in parallel to the amplifier 24. In other such embodiments, the parallel electrical connections may be spaced apart over the pattern of piezoelectric elements 12 so that, when energized, adjacent piezoelectric elements 12 are not vibrating.

Figure 4A:
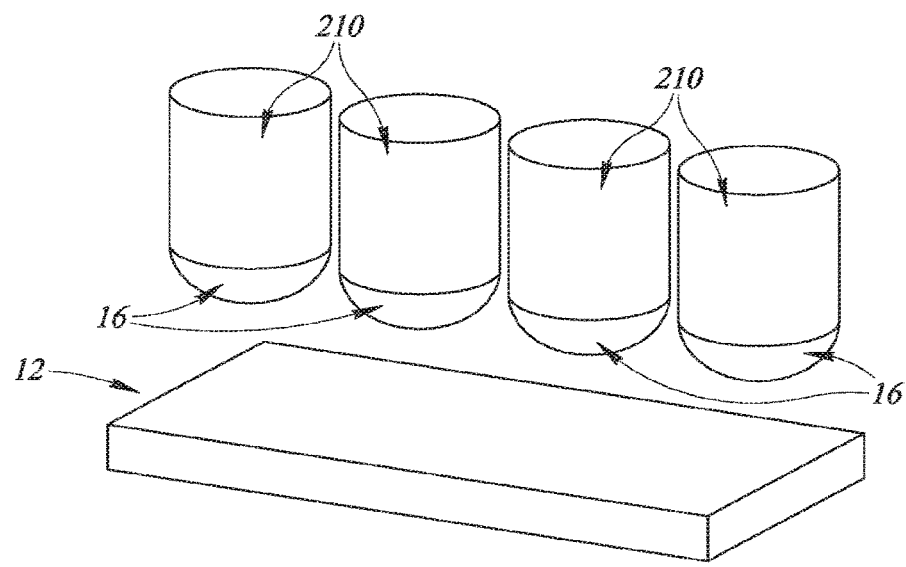
FIG. 4A is a perspective view in partial schematic form of an illustrative piezoelectric element underlying lenses formed in wells of an illustrative microplate.
Figure 4B:
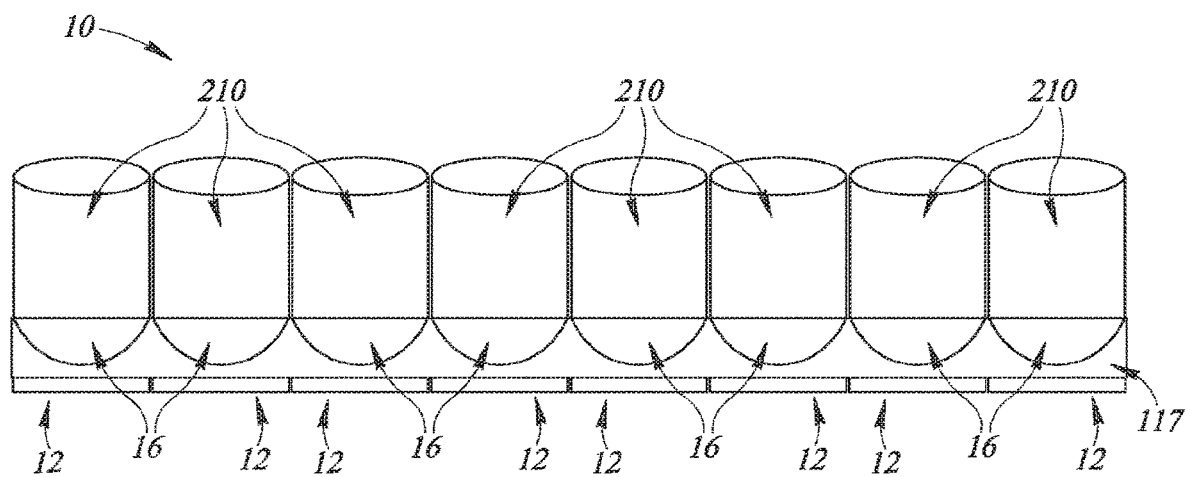
FIGS. 4B and 4D are end plan views in partial schematic form of an array of the piezoelectric elements of FIG. 4A underlying lenses formed in wells of an illustrative microplate.
Figure 4C:
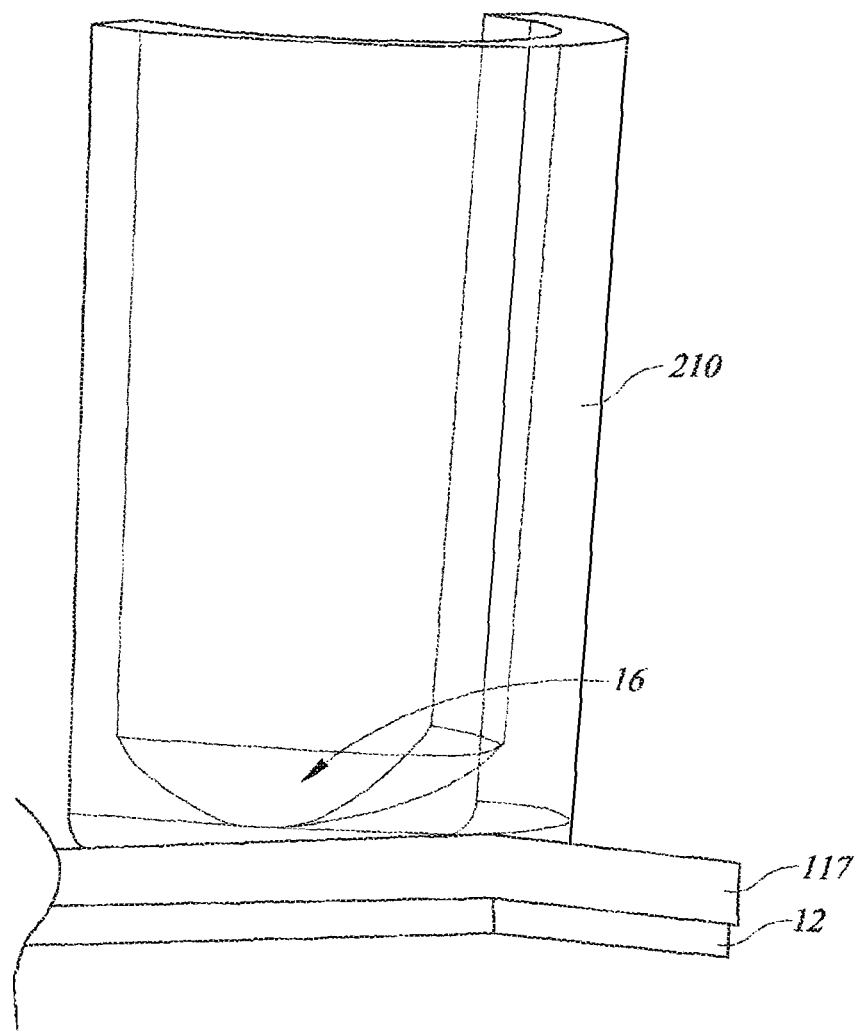
FIG. 4C is a perspective view in partial cutaway of details of a well of a microplate.
Figure 4D:
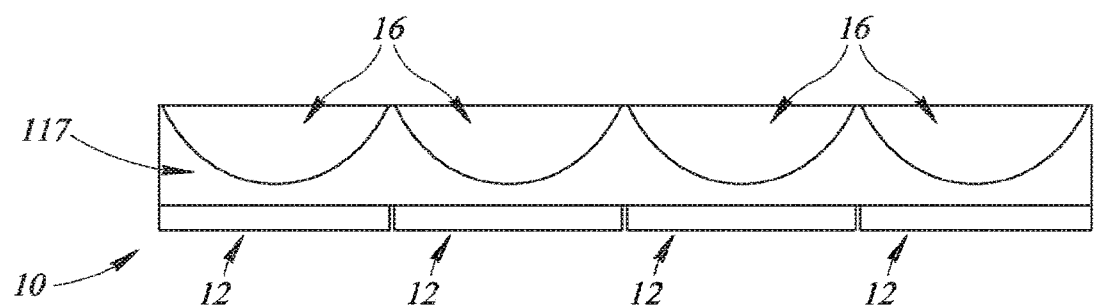

Referring additionally to FIGS. 4A-4E, in other embodiments the lenses 16 may be formed in wells of a microplate 210 instead of being formed in a lens layer that is bonded to the piezoelectric elements 12. As shown in FIGS. 4A, 4B, and 4D, in such embodiments the piezoelectric element array 10 includes the piezoelectric elements 12. Each one of the lenses 16 is formed in single ones of wells 210 of a microplate (not shown).

As shown in FIG. 4C, in such embodiments the bottom of the well 210 can be molded as the lens 16 to focus ultrasound energy into the well 210 and, as such, may not require a separate focusing lens 16 between the piezoelectric element 12 and the bottom of the microplate (as shown in FIGS. 1A-1F, 2A-2C, and 3). As shown in FIG. 4C, the well 210 has the lens 16 integrally formed therein. As shown in FIGS. 4C and 4D, coupling material—that is, transducer fluid 117 (described below)—is positioned between the bottom of the well 210 and the piezoelectric element 12. In various embodiments, the bottom of the well 210 may have a concave shape to act as a lens 16 that focuses ultrasound energy into an interior portion of the well 210. It will be appreciated that the well 210 may be injection-molded to form the lens 16 in its desired shape and focus the ultrasound energy into the desired portion of the well 210. It will also be appreciated that cellular material in the well 210 is sheared due to inertial cavitation occurring in the well 210.

Figure 4E:
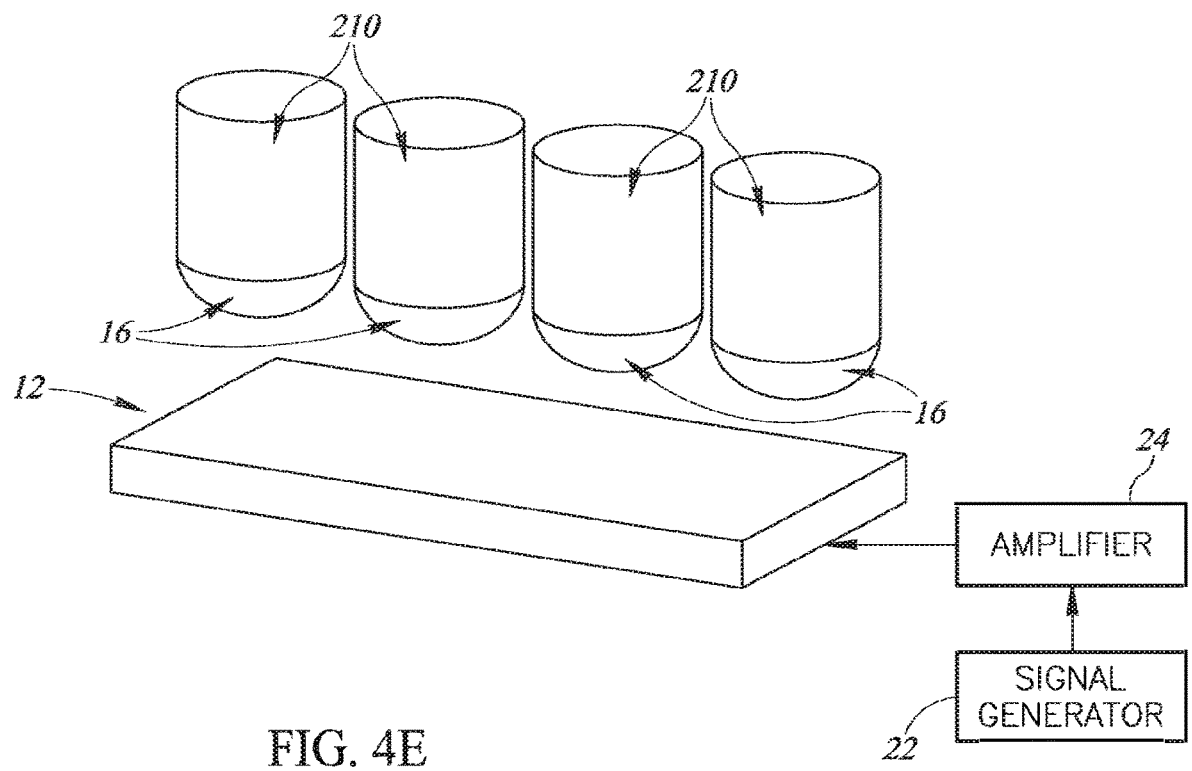
FIG. 4E is an exploded perspective view in partial schematic form of another illustrative system for shearing cellular material.

Referring now to FIG. 4E, in some embodiments the signal generator 22 produces driving signals that are amplified by the amplifier 24 and each piezoelectric element 12 is electrically connected to the amplifier 24. In such embodiments each one of the lenses 16 is formed in single ones of wells 210 of a microplate (not shown).

Now that an introduction to illustrative system environments has been set forth, embodiments of various illustrative system environments will be described by way of non-limiting examples.

Figure 5:
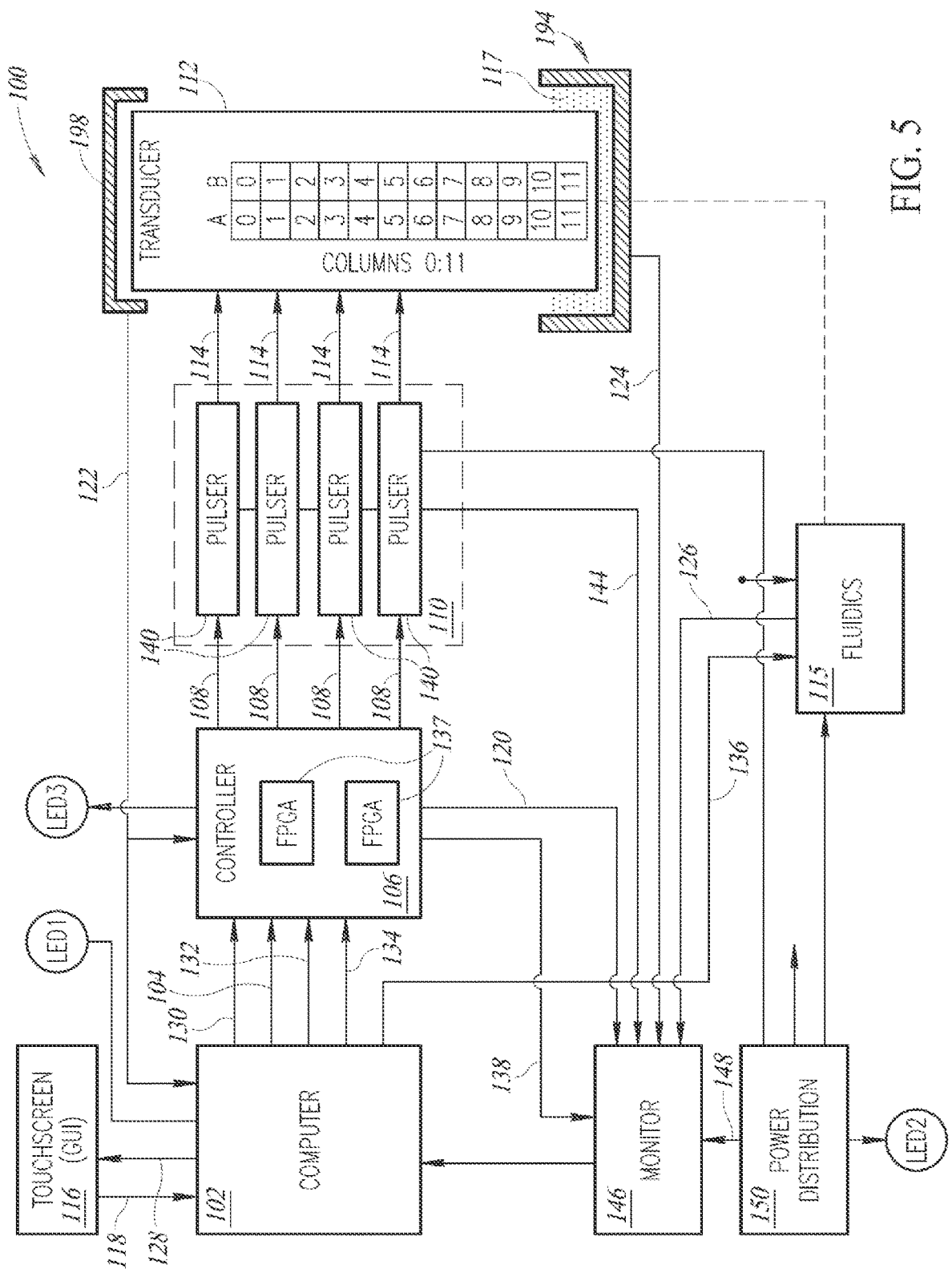
FIG. 5 is a block diagram in partial schematic form of another illustrative system for shearing cellular material.

Referring now to FIG. 5, in various embodiments an illustrative system 100 is provided for shearing cellular material. In some of these embodiments, the system 100 includes the various embodiments of the piezoelectric element array assemblies 10 in which more than one lens 16 overlies a single piezoelectric element 12 (FIGS. 1A-1F, 2A-2C, and 4A-4D). Other embodiments of the system 100 may use any suitable piezoelectric element array assemblies as desired, such as the piezoelectric element array assemblies 10 in which more than one lens 16 overlies a single piezoelectric element 12 and also such as piezoelectric element array assemblies in which only one lens overlies a single piezoelectric element.

Still referring to FIG. 5 and given by way of overview, in some embodiments the system 100 includes the various embodiments of the piezoelectric element array assemblies 10 in which more than one lens 16 overlies a single piezoelectric element 12. In such embodiments, the system 100 includes a computer processor 102 configured to generate timing signals 104. A signal generator 106 is configured to generate ultrasound driving pulses 108 responsive to the timing signals 104. An amplifier 110 is electrically coupled to the signal generator 106 and is configured to amplify the ultrasound driving pulses 108. Piezoelectric elements 12 are arranged in an array 112 of rows and columns (such as without limitation the array 20 shown in FIGS. 2A-2C or the array of piezoelectric elements 10 shown in FIGS. 4B and 4D). It will be appreciated that in various embodiments the array 112 may include 1×N arrays and in some other embodiments may include >1×N arrays (such as, without limitation, 2×2, 2×4, 3×3, and the like). The piezoelectric elements 12 are configured to produce ultrasound energy responsive to amplified driving pulses 114. The timing signals 104 are generated such that adjacent piezoelectric elements 12 are not energized by simultaneous amplified driving pulses 114 and/or temporally sequential amplified driving pulses 114. In some embodiments, a lens layer 14 (FIGS. 1A-1F and 2A-2C) is bonded to the piezoelectric elements 12 (FIGS. 1A-1F and 2A-2C). The lens layer 14 has lenses 16 (FIGS. 1A-1F and 2A-2C) formed therein. In some other embodiments (FIGS. 4A-4D), the lenses 16 (FIGS. 4A-4D) are formed in the wells 210 (FIGS. 4A-4D) of a microplate. More than one of the lenses 16 (FIGS. 1A-1F, 2A-2C, and 4A-4D) overlie single piezoelectric elements 12 (FIGS. 1A-1F, 2A-2C, and 4A-4D) and single lenses 16 (FIGS. 1A-1F, 2A-2C, and 4A-4D) are configured to focus ultrasound energy into single wells of a microplate (not shown).

Still referring to FIG. 5 and still given by way of overview, in some embodiments the system 100 may use any suitable piezoelectric element array assemblies as desired, such as the piezoelectric element array assemblies 10 (FIGS. 1A-1F, 2A-2C, and 4A-4D) in which more than one lens 16 overlies a single piezoelectric element 12 and also such as piezoelectric element array assemblies in which only one lens overlies a single piezoelectric element. In such embodiments, the system 100 includes a housing (not shown in FIG. 5). The signal generator 106 is disposed in the housing and is configured to generate the ultrasound driving pulses 108. The amplifier 110 is disposed in the housing and is electrically coupled to the signal generator 106, and the amplifier 110 is configured to amplify the ultrasound driving pulses. The piezoelectric element array 112 is disposed in the housing. The piezoelectric element array 112 includes at least one piezoelectric element configured to produce ultrasound energy responsive to the amplified driving pulses 114. Lenses are configured to focus ultrasound energy into wells of a microplate. A fluidics system 115 is configured to flow therein a transducer fluid 117 that ultrasonically couples the piezoelectric elements and a microplate. In various embodiments, the transducer fluid 117 may include any suitable fluid, such as without limitation a solution of a surfactant and water. It will be appreciated that, in some embodiments, a surfactant can wet the bottom of the microplate so that bubbles do not form there and possibly block the ultrasound energy from entering the sample contained in the well. A seal (not shown in FIG. 5) is disposed on the housing. The seal is configured to receive a microplate in sealing engagement thereon such that the piezoelectric elements, the housing, and a microplate received in sealing engagement on the seal define a chamber in hydraulic communication with the fluidics system 115 and configured to contain therein the transducer fluid 117.

Now that an overview of various embodiments of the system 100 have been set forth, details will be explained below by way of illustrative, non-limiting examples. Functional details will be addressed first, followed by mechanical details.

Still referring to FIG. 5, in various embodiments a user interface 116 is electrically coupled to the computer processor 102. The user interface may include a graphical user interface, such as any suitable, commercially available touchscreen. The user interface 116 displays information to a user and accepts the user response(s) to the displayed information, thereby permitting a user to set up and control the system 100. In various embodiments, via the user interface 116 a user may enter information such as without limitation: process selection (such as Chromatin, DNA, or Service protocol); column(s) within the array 112 selected for processing (such as any or all of the columns); processing time (for all selected columns); start process (for all selected columns); pause process (all columns); power levels (for all or a subset of wells); pulse parameters (burst length, column-to-column cycling time, PRF, duty cycle, or a combination of parameters); and Restart or Cancel process (while in a paused state). In various embodiments, the user interface 116 may display to a user parameters such as without limitation: device state (which is inherent in the displayed information); process selected; column(s) selected; processing time selected; process time elapsed/remaining (progress indicator) during processing; and process complete indication.

In various embodiments the computer processor 102, via the user interface 116, displays device states and options to the user and receives user inputs. It will be appreciated that the computer processor 102 is disposed in a housing (discussed below). That is, the computer processor 102 is integrated into the system 100 instead of being a stand-alone unit, such as a laptop or desktop computer, that resides outside the physical boundaries of the system 100. The computer processor 102 also configures the system 100 for operation, controls the overall process timing, initiates processes, pauses processes, resumes processes, and monitors state of the system 100. The computer processor 102 suitably is any commercially available computer processor. Given by way of non-limiting example, in various embodiments the computer processor may be a Linux-based computer processor such as, for example, Raspberry Pi (a single board computer processor). In various embodiments, the computer processor 102 controls the following process parameters: which column(s) is(are) active; processing time; pulse parameters; and the functions ON (enables output waveform), PAUSE (pauses output waveform), RESUME (resumes output waveform timing), and CANCEL cancels process and resets timing and returns to menu state). In various embodiments the computer processor 102 receives the following inputs: user input signals 118 from the user interface 116; a signal 120 from the signal generator 106 for heartbeat (to indicate normal operation of the signal generator 106)/watchdog (to prevent the signal generator 106 from elapsing or timing out; a safety interlock state signal 122 (discussed below); a transducer fluid level monitoring signal 124 (discussed below); and a transducer fluid temperature monitoring signal 126 (discussed below). In various embodiments, the computer processor 102 provides the following outputs: a display interface signal 128 supplied to the user interface 116; a column enable signal 130 for activating selected columns; a waveform selection (that is, the timing) signal 104; an Output ON or Output OFF signal 132; a reset waveform sequencer controller timing signal 134 that resets the timing of the signal generator 106; pulse parameters; and a fluidics control signal 136 (discussed below).

In various embodiments, the signal generator 106 generates waveforms (that is, the driving pulses 108) to drive the amplifier 110. The signal generator 106 also gates the driving pulses 108 to specific column(s) of the array 112 based on the column selected and the safety interlock being engaged (via the safety interlock state signal 122). In various embodiments the signal generator 106 suitably may be a commercial off-the-shelf field-programmable gate array (FPGA)-based module. In some embodiments the signal generator 106 may include multiple FPGA modules 137 (depending on FPGA capacity). In embodiments in which the signal generator 106 includes more than one FPGA module, then the number of FPGA modules may equal the number of amplifier modules (discussed below) to simplify the architecture. In various embodiments the signal generator receives the following inputs: the column enable signal 130 for activating selected columns; the waveform selection (that is, the timing) signal 104; the Output ON or Output OFF signal 132; the reset waveform sequencer controller timing signal 134 that resets the timing of the signal generator 106; and the safety interlock state signal 122. In various embodiments the signal generator provides the following outputs: waveforms (that is, the driving pulses 108); the heartbeat/watchdog signal 120; and a waveform counter signal 138 that indicates current output elapsed time.

In various embodiments the amplifier 110 incorporates a suitable number of pulser modules 140 as determined by the number of piezoelectric elements in the array 112 and by the number of channels per pulser module 140. The amplifier 110 generates transducer drive waveforms (that is, the amplified driving pulses 114) with timing equal to the respective input column waveform (that is, the driving pulses 108). The amplifier 110 may also provide a matching network to provide for integrated tuning—that is, low pass filtering to limit radiated electromagnetic interference (EMI) and/or other filtering or impedance matching elements, thereby helping to result in increased power transfer for the transducers of the array 112. The amplifier 110 also integrates voltage waveforms (that is, the amplified driving pulses 114) at the output of the amplifier 110. In various embodiments, the amplifier 110 receives the following inputs: the differential waveform (that is, the driving pulses 108) for the pulser channels; and a single high voltage supply to bias the pulser modules 140. In various embodiments, the amplifier 110 provides the following outputs: the high power waveform for the transducer columns (that is, the amplified driving pulses 114); and an analog voltage proportional to the integrated voltage to the transducer column (that is, proportional to the amplified driving pulses 114) that is provided to the computer processor 102 for monitoring and self-diagnostics purposes.

In various embodiments a monitor module 146 suitably receives the watchdog/heartbeat signal 120, the transducer fluid level monitoring signal 124, the transducer fluid temperature monitoring signal 126, the waveform counter signal 138, the analog voltage 144, and voltages 148 (from a power distribution module 150 that converts mains power into direct current power for the components of the system 100) and provides them to the computer processor 102. The monitor module 146 includes suitable circuitry and logic for performing self-diagnostics functions for the system 100.

Figure 6:
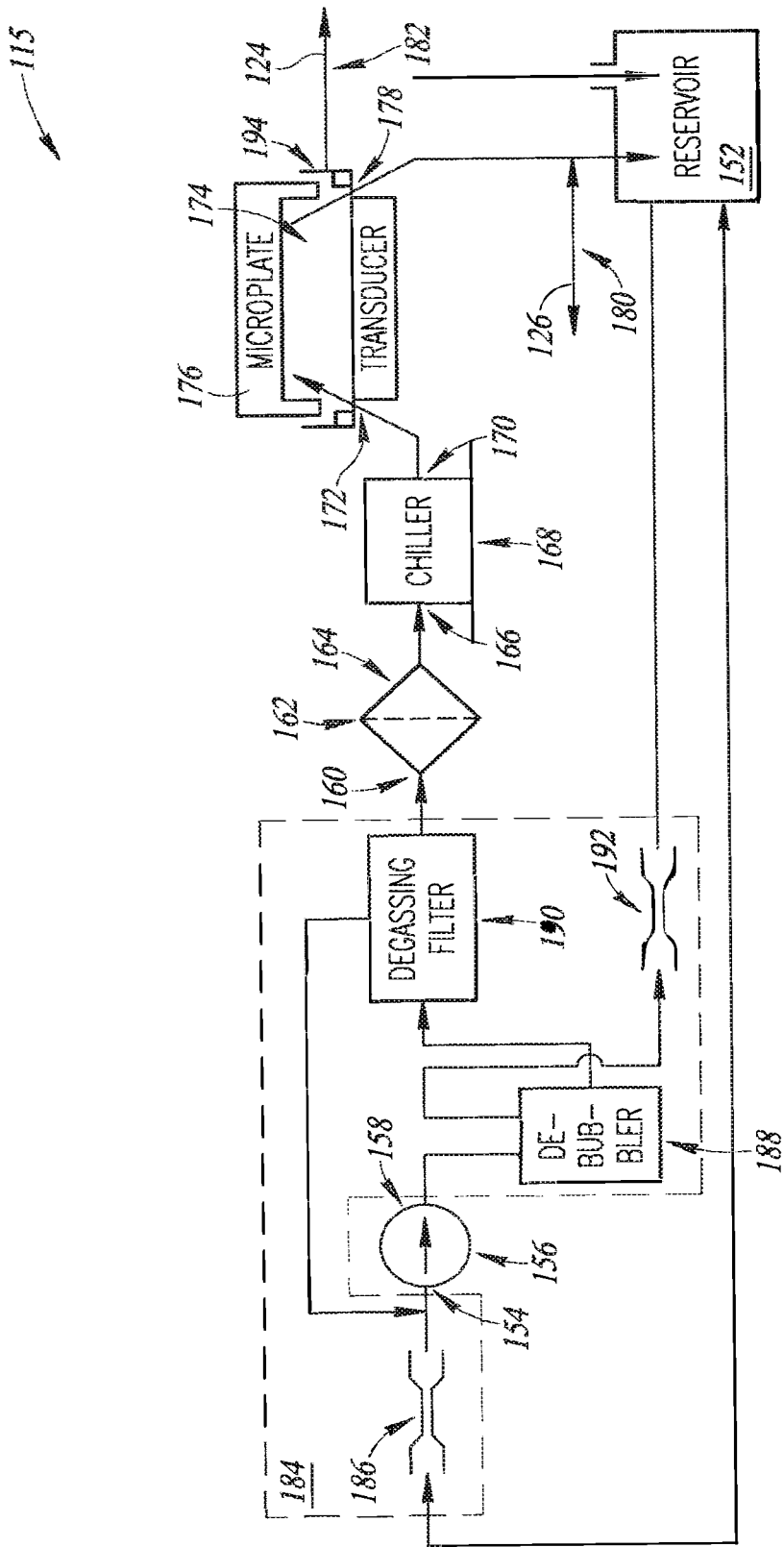
FIG. 6 is a piping diagram in partial schematic form of details of a fluidics system of the system of FIG. 5.

Referring additionally to FIG. 6, in various embodiments the fluidics system 115 chills and circulates the transducer fluid 117 for coupling the ultrasound energy from the piezoelectric elements and lenses to the wells of a microplate. It will be appreciated that all components of the fluidics system 115 are disposed within one housing (not shown in FIG. 6 but discussed below)—as are all components of the system 100.

In various embodiments a reservoir 152 is configured to receive and store transducer fluid 117. A suction port 154 of a pump 156 is hydraulically coupled to the reservoir 152 to receive transducer fluid 117. The fluidics control signal 136 is supplied to control circuitry (not shown) of the pump 156, and state of flow in the fluidics system 115 (that is, forward, off, or reverse) suitably is controlled by the fluidics control signal 136. A discharge port 158 of the pump 156 is hydraulically coupled to an inlet port 160 of a suitable filter 162, such as without limitation a particle filter. An outlet port 164 of the filter 162 is hydraulically coupled to an inlet port 166 of a suitable chiller 168, such as without limitation a thermo-electric device like a peltier cooler. State of the chiller (that is, chiller on or chiller off) suitably is controlled by the fluidics control signal 136. An outlet port 170 of the chiller 168 is hydraulically coupled to an inlet port 172 of a well 174 that contains therein transducer fluid 117 for coupling the ultrasound energy from the piezoelectric elements and lenses to the wells of a microplate 176. An outlet port 178 of the well 174 is hydraulically coupled to the reservoir 152. A temperature probe 180 provides the transducer fluid temperature monitoring signal 126 to the monitor module 146 (FIG. 5) as monitored at an outlet of a processing tray 194. A fluid level probe 182 in the processing tray 194 provides the transducer fluid level monitoring signal 124 to the monitor module 146 (FIG. 5). The fluid level probe 182 is configured to monitor level of transducer fluid 117 in the processing tray 194 to help ensure that a sufficient amount of transducer fluid 117 is contained in the processing tray 194 to ultrasonically couple the microplate 176 and the piezoelectric elements. While flow impedance between the well 174 and the reservoir 152 is maintained low, a seal (discussed below) between the microplate 176 and the processing tray 194 can help to facilitate higher flow rates of the transducer fluid 117.

It will be appreciated that, in some embodiments, debubbling and degassing of the transducer fluid 117 is not required. It will also be appreciated that, in some other embodiments, debubbling and degassing of the transducer fluid 117 may be desired. In such embodiments in which debubbling and degassing of the transducer fluid 117 may be desired, optional debubbling and degassing components 184 may be interposed in the fluidics system 115. As shown in FIG. 5, the optional debubbling and degassing components 184 may include: a restrictor 186 interposed between the reservoir 152 and the suction port 154 of the pump 156; a debubbler 188 hydraulically coupled to the discharge port 158 of the pump 156; a degassing filter 190 interposed between the debubbler 188 and the inlet port 160 of the filter 162; and a restrictor 192 interposed between the debubbler 188 and the reservoir 152.

Mechanical/fluidics aspects will be discussed next, followed by a discussion of functionality and operation of various embodiments of the system 100.

Referring additionally to FIGS. 7A-7E, in various embodiments of the system 100 all components of the system 100 are disposed in a housing 196. The housing may be made of any suitable material as desired, such as plastic, metal, or the like. In some embodiments the housing 196 may function as a faraday shield. In some such embodiments the housing 196 may be made of plastic and lined with either a continuous covering of conductive material (not shown) or a mesh of conductive material (not shown). In such embodiments, an external electrical field causes electric charges within the conductive material that lines the housing 196 to be distributed such that the distributed electric charges cancel the electric field's effect in the interior of the housing 196, thereby helping to protect electronic components of the system 100 from external radio frequency interference—and vice versa.

In various embodiments the housing includes a lid 198. In various embodiments the lid 198 is configured to open and close, such as by being rotated upwardly and downwardly, respectively, about a hinged axis disposed at an edge of the lid 198 toward a central part of the housing 196. The lid 198 and an associated sunken portion 200 (FIGS. 7B and 7C) defined in the housing 196 are sized such that the microplate 176 can be received in the sunken portion 200 when the lid 198 is open. Closing the lid 198 (which means that a user has no access to the acoustic field) causes the safety interlock state signal 122 (FIGS. 5 and 6) to be active. As a result, processing may be enabled. Opening the lid 198 (which means that a user has access to the acoustic field) causes the safety interlock state signal 122 (FIGS. 5 and 6) to be inactive. As a result, processing is not enabled.

Figure 7A:
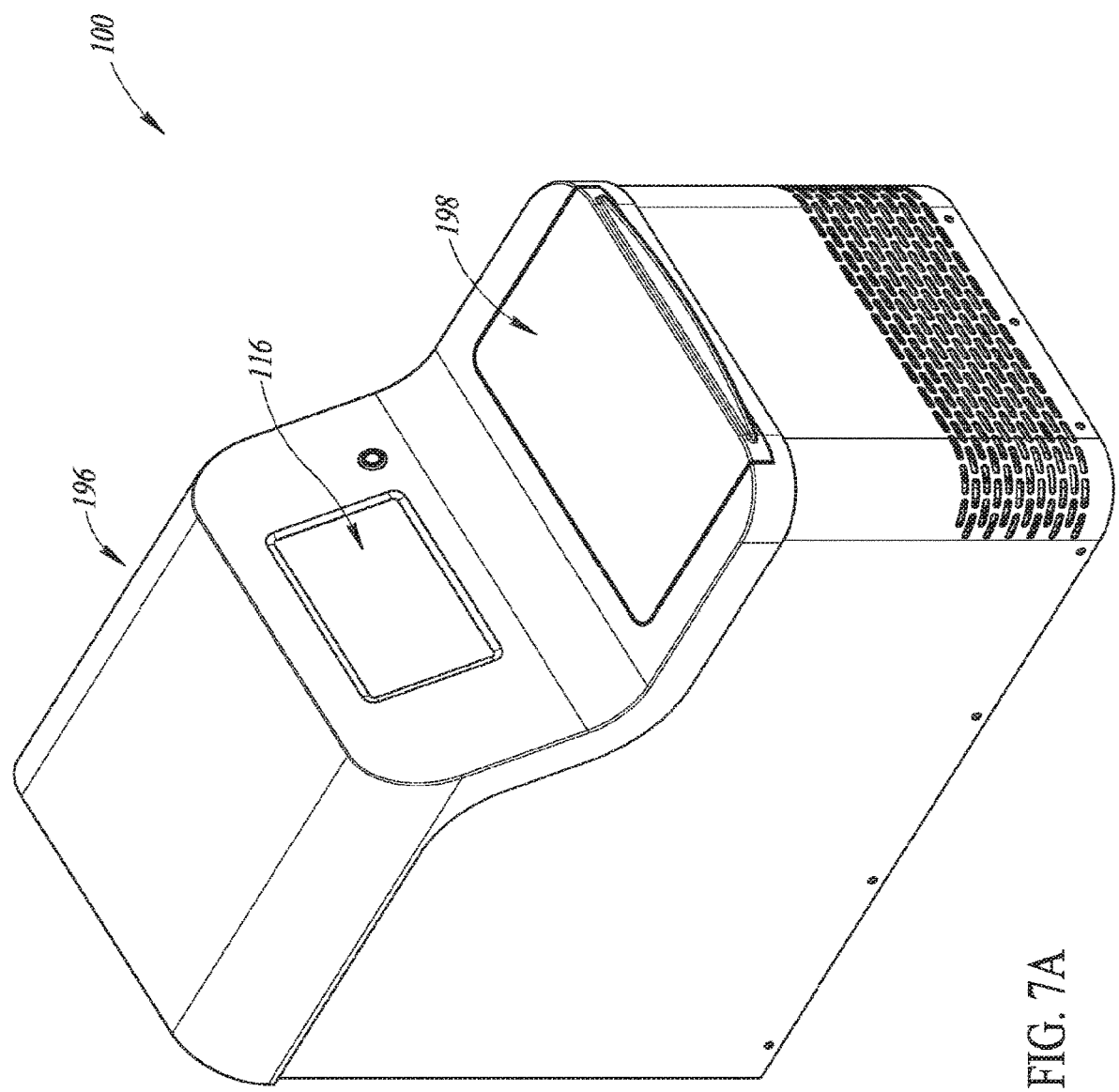
FIG. 7A is a perspective view of an illustrative system for shearing cellular material.
Figure 7B:
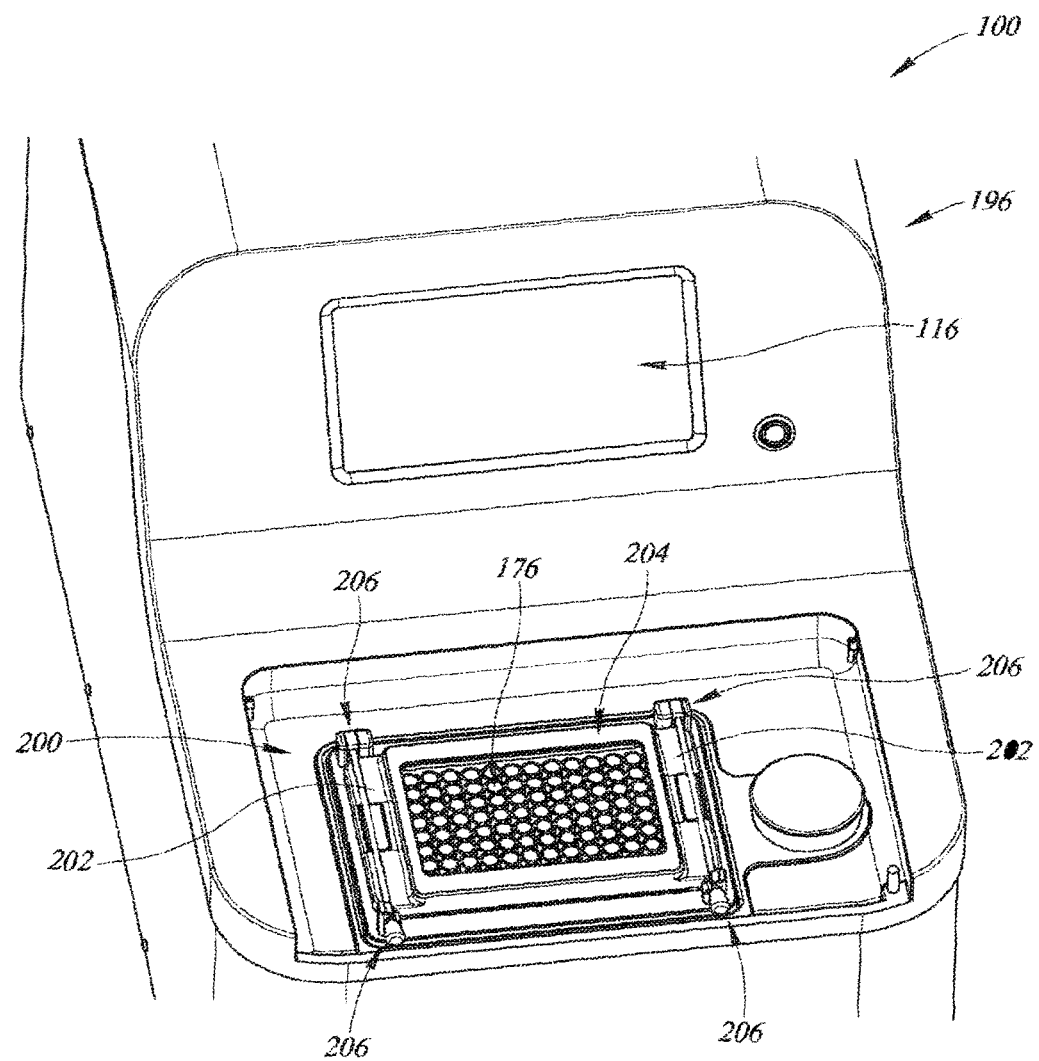

In various embodiments and as shown in FIGS. 7B and 7C, a seal 202 is disposed on a top surface of the housing 196 within the sunken portion 200. An opening (not shown) is defined in the top surface of the housing 196 within the sunken portion 200 and the seal 202 surrounds the opening. The seal 202 is sized to receive thereon the microplate 176. A hold-down frame 204 is placed on top of the microplate 176. Each of a pair of clamps 206 urges a side of the hold down frame 204 onto the microplate 176 in sealing engagement with the seal 202. Thus, the housing 196, the seal 202, the microplate 176, the hold-down frame 204, and the clamps 206 cooperate to hydraulically seal the opening defined in the top surface of the housing 196 within the sunken portion 200.

In some embodiments, the hold down frame 204 and the clamps 206 may be integrated into an underside of the lid 198. In such embodiments, closing the lid 198 applies the force entailed to cause the clamps 206 to sealingly engage the housing 196, the seal 202, the microplate 176, and the hold-down frame 204. Conversely, opening the lid 198 causes the clamps 206 to disengage engage the housing 196, the seal 202, the microplate 176, and the hold-down frame 204 from sealing engagement, thereby permitting removal of the microplate 176.

Figure 7D:
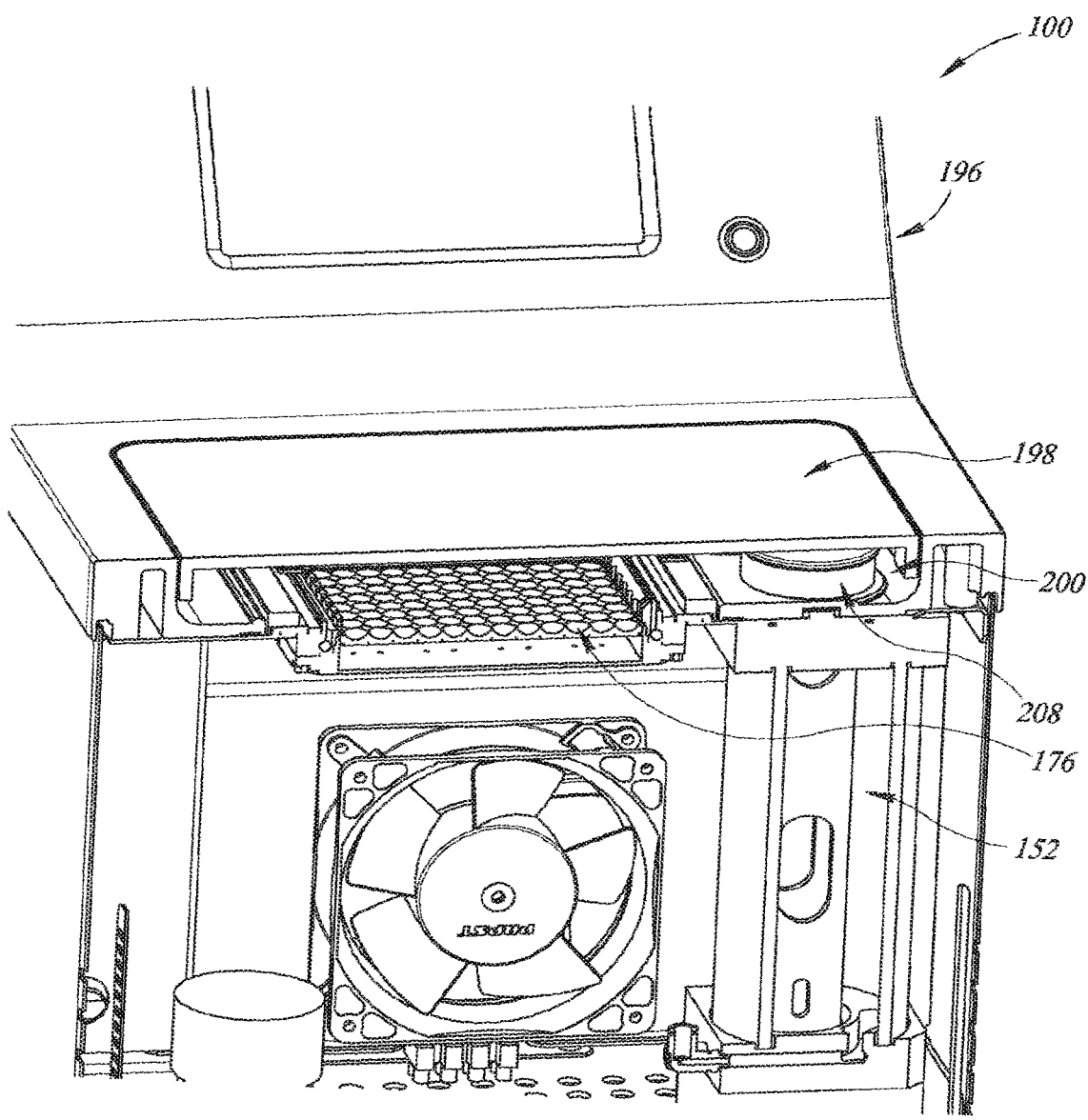

In various embodiments and as shown in FIG. 7D, the reservoir 152 is sealed and filled with a lid 208 that is received on a top portion of the reservoir 152 (such as by being threadedly received or press fit). The lid is accessible in the sunken portion 200 of the housing 196. In some embodiments, the reservoir 152 may include a level indicator device, such as without limitation an integrated sight glass/tube or the like, to provide indication to a user regarding level of transducer fluid 117 in the reservoir 152. If desired, a sensor may provide a user with knowledge about when to refill the reservoir 152.

Figure 7E:
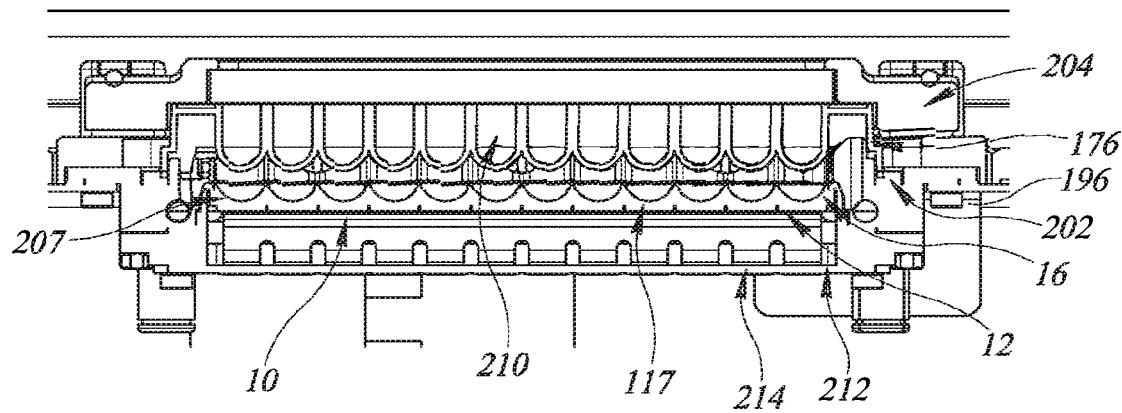
FIG. 7E is a front plan view in partial cutaway of details of the system of FIG. 7A.
Figure 7F:
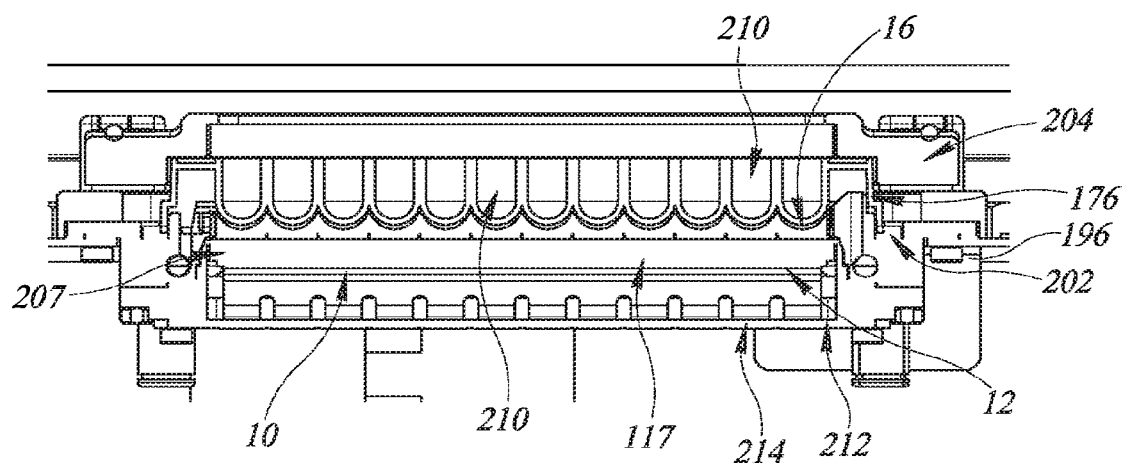
FIG. 7F is a front plan view in partial cutaway of details of another embodiment of the system of FIG. 7A.

In various embodiments and as shown in FIGS. 7E and 7F, the seal 202 holds down the microplate 176 and the clamps 206 hold down the seal 202. Transducer fluid 117 in a gap 207 between the lenses 16 and the microplate 176 ultrasonically couples the piezoelectric elements 12 with wells 210 of the microplate 176. The array 112 is attached to a base frame 212 that is, in turn, attached to the housing 196. A printed circuit board interface 214 electrically couples the piezoelectric elements 12 to cables (not shown) that electrically conduct the amplified driving pulses 114 from the amplifier 110.

In various embodiments of the system 100, no transducer fluid 117 is in the gap 207. After the microplate 176 is sealingly engaged by the clamps 206 to the seal 202 and the lid 198 is shut, transducer fluid 117 is pumped into the gap 207 from the reservoir 152 by the pump 156. Placing the microplate 176 onto a bath-like structure with no transducer fluid initially disposed therein and then filling the gap 207 with transducer fluid 117 only after the microplate 176 has been placed thereon flies in the face of conventional systems in which a microplate is placed into a bath of transducer fluid. As a result, embodiments of the system 100 help provide more secure placement of the microplate 176 than in conventional systems and can help to reduce the possibility of transducer fluid 117 getting into the wells 210 of the microplate 176, thereby helping to reduce the possibility of contaminating contents of the wells 210 with transducer fluid 117.

When the lid 198 is shut, the safety interlock is engaged and the safety interlock state is active (via the safety interlock state signal 122). The microplate 176 is sealingly engaged with the housing 196. Processing of samples can proceed as discussed below.

Referring now to FIGS. 1A-1F, 2A-2C, 3, 4A-4D, 5-6, 7A-7F, and 8A-8E, functionality and operation of various embodiments of the system 100 will be explained by examples provided by way of illustration and not of limitation.

Regarding control of embodiments of the system 100, the computer processor 102 is the center of control for the system 100. The computer processor 102 outputs display to the user interface 116 and reads user input that is input via the user interface 116. In addition, the computer processor 102 sets up the signal generator 106 with respect to which processing regimen is to be run. The computer processor 102 directly controls which channels are active, the overall processing time, starting the process, and stopping the process.

Waveform timing for driving the piezoelectric elements 12 output by the signal generator as the driving pulses 108. In some embodiments of the system 100 with a ninety-six well microplate 176, four lenses 16 overlie each piezoelectric element 12, and the array 112 includes twenty-four piezoelectric element array assemblies 10. In some embodiments, the number of pulser modules 140 may be equal to the number of piezoelectric elements 10, and in some other embodiments the number of pulser modules 140 may be equal to half the number of piezoelectric elements 10.

As discussed above, for the waveform (that is, the driving pulses 108) to be output, the lid 198 must be closed. When the lid 198 is open, both the computer processor 102 and the signal generator 106 do not allow the output (that is, the driving pulses 108) to be driven. This is because the safety interlock state signal 122 is input to both the computer processor 102 and the signal generator 106. In addition, the computer processor 102 monitors both the transducer fluid temperature (via the transducer fluid temperature monitoring signal 126) and the transducer fluid level (via the transducer fluid level monitoring signal 124). If the temperature of the transducer fluid 117 is above an acceptable level or the transducer fluid 117 does not fully bridge the gap 207 between the piezoelectric elements 12 and the wells 210, then the output of the signal generator 106 will not be enabled. For output of the signal generator 106 to be enabled, the following three conditions must be met: (i) safety interlock state active (that is, the lid 198 is closed); (ii) temperature of transducer fluid 117 is below a threshold temperature; and (iii) level of transducer fluid 117 in the gap 207 is above minimum level. However and notwithstanding the above, it will be appreciated that in some embodiments it may be desirable to allow testing to make measurements with the lid 198 open. In such embodiments, an engineering mode can permit operation with the lid 198 open.

In various embodiments of the system 100, waveform timing may result in simultaneous and/or sequential driving pulses 108 that do not energize adjacent piezoelectric elements 12 in the array 112, thereby allowing a piezoelectric element 12 (and adjacent piezoelectric elements 12) to cool down for a period of time before that same piezoelectric element 12 is energized again. Waveform timing for embodiments of the system 100 will be discussed by way of a non-limiting example for an embodiment of the system 100 with a ninety-six well microplate 176, four lenses 16 overlie each piezoelectric element 12, and the array 112 includes twenty-four piezoelectric element array assemblies 10. However, it will be appreciated that similar waveform timing may be applied to any embodiment of the system 100 in which more than one lens 16 overlies a single piezoelectric element 12.

Figure 8A:
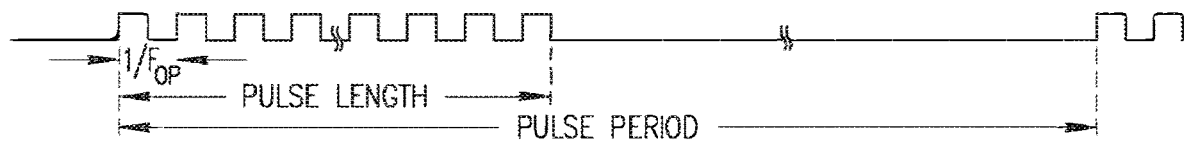
FIGS. 8A-8D illustrate details of waveform timing of the system of FIG. 5.

Given by way of non-limiting example and referring additionally to FIG. 8A, the acoustic waveform that performs the shearing operation (that is, the acoustic waveform of the amplified driving pulses 114) is high amplitude and highly non-linear, as the shearing is primarily a function of cavitation. The basic waveform timing is shown in FIG. 8A.

Figure 8B:
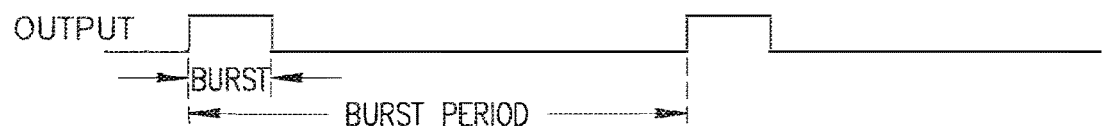

Referring additionally to FIG. 8B, the pulsed acoustic waveform is applied to a column of wells 210 for N Pulses. Then, the column of wells 210 is allowed to cool before another burst is applied to the column. The Burst length is equal to an integer number of contiguous Pulse periods with output acoustic power. Architecturally, the Burst period is equal to six times the Burst length, since there are two of the twelve columns being processed at a given time. The overall processing time is an integer multiple of the Burst period.

Figure 8C:
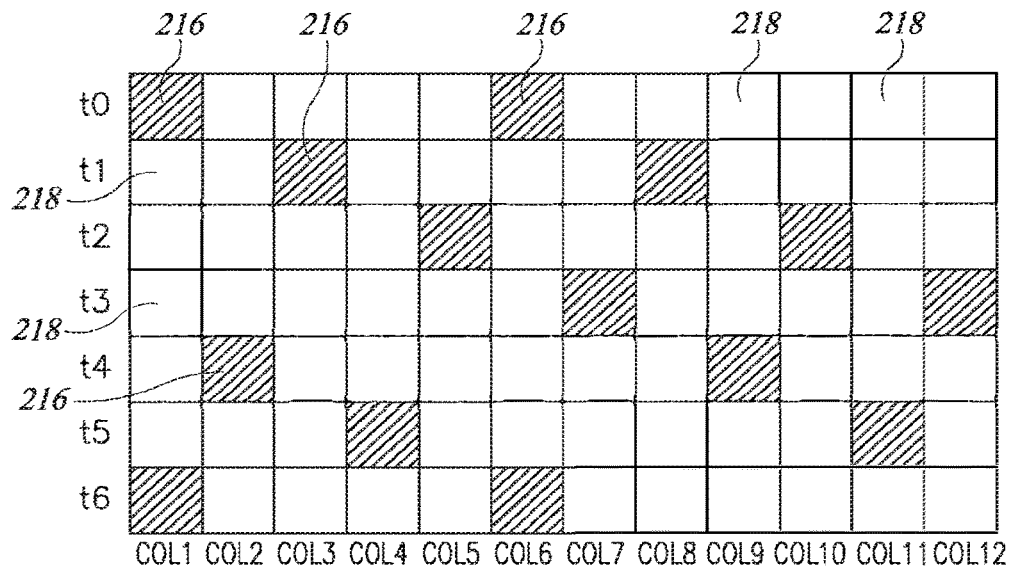

Referring additionally to FIG. 8C, timing of applied acoustic power to the respective columns is shown, where t0 through t6 (rows) represent a single Burst period, and COL1 through COL12 (columns) represent the twelve columns of the microplate 176. A shaded square 216 indicates acoustic power output (Burst) and a white square 218 indicates a cool down period. It will be appreciated that FIG. 8C shows that adjacent piezoelectric elements 12 are not energized simultaneously (that is, in any single row representing a single Burst period) and are not energized by sequential waveforms (that is, in any given row that represents a given Burst period and in a row directly underneath the given row, representing a sequential Burst period).

Figures 8D, 8E:
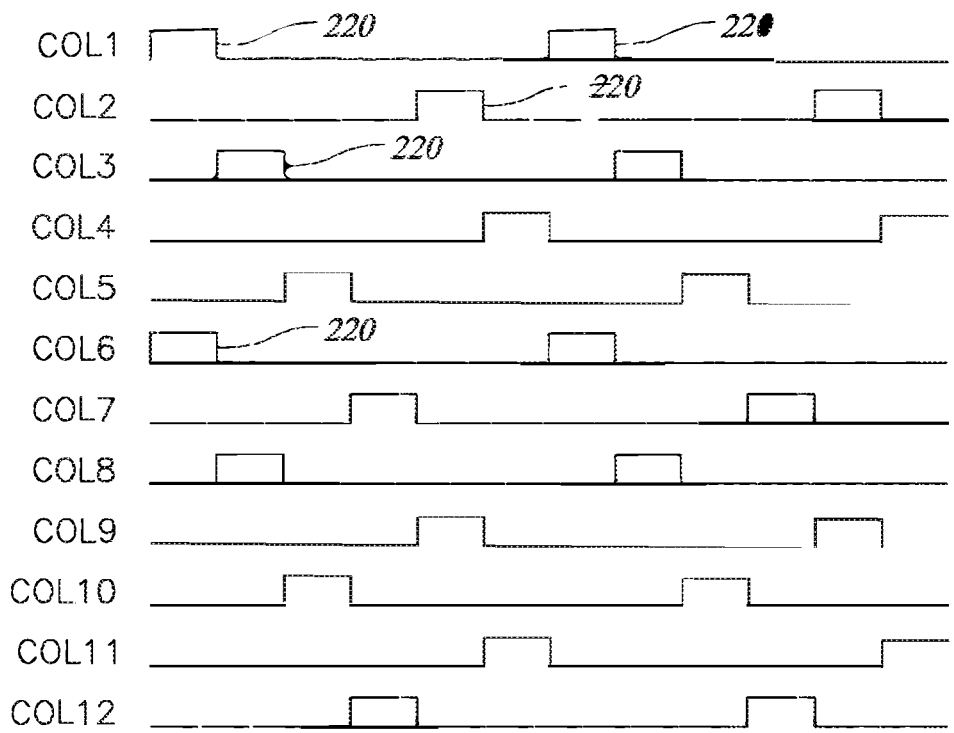
FIG. 8E illustrates further details of the system of FIG. 5.

Referring additionally to FIG. 8D, relative timing of applied acoustic power is shown for the twelve columns where high amplitude 220 represents the Burst for a given column. Thus, in FIG. 8D the high amplitudes correspond to the shaded squares of FIG. 8C. As such, FIG. 8D also shows that adjacent piezoelectric elements 12 may not be not energized simultaneously and may not be energized by sequential waveforms.

For example and as shown in FIGS. 8C and 8D, it will be appreciated that the Burst for COL1 occurs at t0. A simultaneous Burst at t0 applies acoustic power to COL6—which is not adjacent to COL1. Moreover, the Burst at t1 applies acoustic power to COL3 and COL8—neither of which are adjacent to COL1. Further, the soonest that a Burst applies acoustic power to a column adjacent COL1 is at t4—when acoustic power is applied to COL2. As a result, this timing technique can help to reduce heating.

Referring additionally to FIG. 8E, mapping of the twenty-four channels of the pulser modules 140 to the piezoelectric elements 12 are shown. Again, it will be appreciated that any number of the pulser modules 140 with any number of channels per pulser module 140 may be used as desired. For example, in some embodiments twenty-four channels of the pulser modules 140 may be implemented with eight pulser modules 140 having three channels apiece. However, it will be appreciated that it is not necessary to process ninety-six samples and any number of samples may be processed as desired. Accordingly, fewer than ninety-six wells may be processed as desired for a particular application. That is, in some embodiments as few as one well may be processed and in some other embodiments as many as ninety-six wells may be processed. In such embodiments, wells that do not contain samples for processing would be filled with water or another liquid that does not contain samples to be processed.

Various example embodiments of the disclosed subject matter can be described in view of the following clauses:

1. A piezoelectric element array assembly comprising: at least one piezoelectric element configured to produce ultrasound energy responsive to amplified driving pulses; and a lens layer bonded to the at least one piezoelectric element, the lens layer having a plurality of lenses formed therein that are configured to focus ultrasound energy created by single ones of the at least one piezoelectric element into a plurality of wells of a microplate disposable in ultrasonic communication with the lens layer, wherein more than one of the plurality of lenses overlie single ones of the at least one piezoelectric element.

2. The piezoelectric element array assembly of Clause 1, wherein the at least one piezoelectric element includes a column of two piezoelectric elements.

3. The piezoelectric element array assembly of Clause 1, wherein the at least one piezoelectric element includes a column of four piezoelectric elements.

4. The piezoelectric element array assembly of Clause 1, wherein the at least one piezoelectric element includes a column of six piezoelectric elements.

5. The piezoelectric element array assembly of Clause 1, wherein the at least one piezoelectric element includes a column of eight piezoelectric elements.

6. The piezoelectric element array assembly of Clause 1, wherein the at least one piezoelectric element includes a column of twelve piezoelectric elements.

7. The piezoelectric element array assembly of Clause 1, wherein four lenses overlie single ones of the at least one piezoelectric element.

8. The piezoelectric element array assembly of Clause 1, wherein the at least one piezoelectric element is made of a material including lead zirconate titanate.

9. The piezoelectric element array assembly of Clause 1, wherein the lens layer is made of a material having an acoustic impedance between acoustic impedance of the at least one piezoelectric element and a coupling fluid that is disposable between the lens layer and a microplate.

10. The piezoelectric element array assembly of Clause 1, wherein the lens layer is made of a material chosen from graphite and fluorphlogopite mica in a borosilicate glass matrix.

11. A method of fabricating a piezoelectric element array assembly, the method comprising: providing at least one piezoelectric element configured to produce ultrasound energy responsive to amplified driving pulses; and bonding a lens layer to the at least one piezoelectric element, the lens layer having a plurality of lenses formed therein that are configured to focus ultrasound energy created by single ones of the at least one piezoelectric element into a plurality of wells of a microplate disposable in ultrasonic communication with the lens layer, wherein more than one of the plurality of lenses overlie single ones of the at least one piezoelectric element.

12. The method of Clause 11, wherein the at least one piezoelectric element includes a column of two piezoelectric elements.

13. The method of Clause 11, wherein the at least one piezoelectric element includes a column of four piezoelectric elements.

14. The method of Clause 11, wherein the at least one piezoelectric element includes a column of six piezoelectric elements.

15. The method of Clause 11, wherein the at least one piezoelectric element includes a column of eight piezoelectric elements.

16. The method of Clause 11, wherein the at least one piezoelectric element includes a column of twelve piezoelectric elements.

17. The method of Clause 11, wherein four lenses overlie single ones of the at least one piezoelectric element.

18. A system for shearing cellular material, the system comprising: a signal generator configured to generate ultrasound driving pulses; an amplifier electrically coupled to the signal generator and configured to amplify the ultrasound driving pulses; a piezoelectric element array including at least one piezoelectric element configured to produce ultrasound energy responsive to amplified driving pulses; and a plurality of lenses, wherein more than one of the plurality of lenses overlie single ones of the at least one piezoelectric element and wherein single ones of the plurality of lenses are configured to focus ultrasound energy into single ones of a plurality of wells of a microplate.

19. The system of Clause 18, further comprising: a lens layer bonded to the at least one piezoelectric element, the lens layer having the plurality of lenses formed therein.

20. The system of Clause 18, wherein single ones of the plurality of lenses are formed in single ones of a plurality of wells in a microplate.

21. The system of Clause 18, wherein the at least one piezoelectric element includes a column of two piezoelectric elements.

22. The system of Clause 18, wherein the at least one piezoelectric element includes a column of four piezoelectric elements.

23. The system of Clause 18, wherein the at least one piezoelectric element includes a column of six piezoelectric elements.

24. The system of Clause 18, wherein the at least one piezoelectric element includes a column of eight piezoelectric elements.

25. The system of Clause 18, wherein the at least one piezoelectric element includes a column of twelve piezoelectric elements.

26. The system of Clause 18, wherein four lenses overlie single ones of the at least one piezoelectric element.

27. The system of Clause 18, wherein the at least one piezoelectric element is made of a material including lead zirconate titanate.

28. The system of Clause 18, wherein the lens layer is made of a material having an acoustic impedance between acoustic impedance of the at least one piezoelectric element and a coupling fluid that is disposable between the lens layer and a microplate.

29. The system of Clause 18, wherein the lens layer is made of a material chosen from graphite and fluorphlogopite mica in a borosilicate glass matrix.

30. A method comprising: generating ultrasound driving pulses; amplifying the ultrasound driving pulses; producing ultrasound energy with at least one piezoelectric element responsive to the amplified driving pulses; and focusing the ultrasound energy created by single ones of the at least one piezoelectric element into a plurality of wells of a microplate by a plurality of lenses, wherein more than one of the plurality of lenses overlie single ones of the at least one piezoelectric element and wherein single ones of the plurality of lenses are ultrasonically coupled to single ones of the plurality of wells.

31. The method of Clause 30, wherein the plurality of lenses are formed in a lens layer that is bonded to the at least one piezoelectric element.

32. The method of Clause 30, wherein single ones of the plurality of lenses are formed in single ones of a plurality of wells in a microplate.

33. The method of Clause 30, wherein four lenses overlie single ones of the at least one piezoelectric element.

34. A system for shearing cellular material, the system comprising: a computer processor configured to generate timing signals; a signal generator configured to generate ultrasound driving pulses responsive to the timing signals; an amplifier electrically coupled to the signal generator and configured to amplify the ultrasound driving pulses; a plurality of piezoelectric elements arranged in an array of rows and columns and configured to produce ultrasound energy responsive to amplified driving pulses, the timing signals being generated such that adjacent ones of the plurality of piezoelectric elements are not energized by at least amplified driving pulses chosen from simultaneous driving pulses and temporally sequential driving pulses; and a plurality of lenses, wherein more than one of the plurality of lenses overlie single ones of the plurality of piezoelectric elements and wherein single ones of the plurality of lenses are configured to focus ultrasound energy into single ones of a plurality of wells of a microplate.

35. The system of Clause 34, further comprising: a lens layer bonded to the plurality of piezoelectric elements, the lens layer having a plurality of lenses formed therein.

36. The system of Clause 34, wherein single ones of the plurality of lenses are formed in single ones of a plurality of wells in a microplate.

37. The system of Clause 34, wherein the plurality of piezoelectric elements includes a column of two piezoelectric elements.

38. The system of Clause 34, wherein the plurality of piezoelectric elements includes a column of four piezoelectric elements.

39. The system of Clause 34, wherein the plurality of piezoelectric elements includes a column of six piezoelectric elements.

40. The system of Clause 34, wherein the plurality of piezoelectric elements includes a column of eight piezoelectric elements.

41. The system of Clause 34, wherein the plurality of piezoelectric elements includes a column of twelve piezoelectric elements.

42. The system of Clause 34, wherein four lenses overlie single ones of the at least one piezoelectric element.

43. The system of Clause 34, wherein the at least one piezoelectric element is made of a material including lead zirconate titanate.

44. The system of Clause 34, wherein the lens layer is made of a material having an acoustic impedance between acoustic impedance of the at least one piezoelectric element and a coupling fluid that is disposable between the lens layer and a microplate.

45. The system of Clause 34, wherein the lens layer is made of a material chosen from graphite and fluorphlogopite mica in a borosilicate glass matrix.

46. A system for shearing cellular material, the system comprising: a housing; a signal generator disposed in the housing and configured to generate ultrasound driving pulses; an amplifier disposed in the housing and electrically coupled to the signal generator, the amplifier being configured to amplify the ultrasound driving pulses; a piezoelectric element array disposed in the housing, the piezoelectric element array including at least one piezoelectric element configured to produce ultrasound energy responsive to amplified driving pulses; a plurality of lenses configured to focus ultrasound energy into a plurality of wells of a microplate; a fluidics system configured to flow therein a transducer fluid; and a seal disposed on the housing, the seal being configured to receive a microplate in sealing engagement thereon such that the piezoelectric element array, the housing, and a microplate received in sealing engagement on the seal define a chamber in hydraulic communication with the fluidics system and configured to contain therein transducer fluid.

47. The system of Clause 46, further comprising: a lens layer bonded to the at least one piezoelectric element, the lens layer having the plurality of lenses formed therein.

48. The system of Clause 46, wherein single ones of the plurality of lenses are formed in single ones of a plurality of wells in a microplate.

49. The system of Clause 46, further comprising: a clamping mechanism configured to hold a microplate in sealing engagement on the seal.

50. The system of Clause 46, further comprising: an openably closable lid disposed on the housing.

51. The system of Clause 50, further comprising: an interlock device mechanically configured to sense position of the lid, the interlock device being configured to prevent energization of the piezoelectric element array when the lid is in an open position.

52. The system of Clause 46, wherein the fluidics system includes a reservoir disposed in the housing and configured to receive therein transducer fluid.

53. The system of Clause 52, wherein the fluidics system further includes a pump disposed in the housing and configured to cause flow of transducer fluid.

54. The system of Clause 46, wherein the fluidics system includes a debubbling and degassing subsystem.

55. A method of shearing cellular material, the method comprising: placing a microplate with cellular material disposed in a plurality of wells defined therein on a seal disposed on a housing; clamping the microplate on the seal in sealing engagement therewith; flowing transducer fluid in a fluidics system disposed in the housing such that transducer fluid is placed in hydraulic communication with a plurality of lenses; energizing an array of piezoelectric elements to produce ultrasound energy; and focusing ultrasound energy in the plurality of wells with a plurality of lenses such that cavitation is induced in the cellular material disposed in the plurality of wells.

56. The method of Clause 55, wherein the plurality of lenses are formed in a lens layer that is bonded to the array of piezoelectric elements.

57. The method of Clause 55, wherein single ones of the plurality of lenses are formed in single ones of the plurality of wells.

58. The method of Clause 55, further comprising: opening a lid in the housing before placing the microplate with cellular material disposed in the plurality of wells defined therein on the seal disposed on the housing; and shutting the lid after clamping the microplate on the seal in sealing engagement therewith.

59. The method of Clause 58, further comprising: satisfying an interlock condition that permits causing transducer fluid to flow in the fluidics system and that permits energizing the array of piezoelectric elements responsive to shutting the lid after clamping the microplate on the seal in sealing engagement therewith.

60. The method of Clause 55, wherein: more than one of the plurality of lenses overlie single ones of the plurality of piezoelectric element; and single ones of the plurality of lenses are configured to focus ultrasound energy into single ones of the plurality of wells of the microplate.

61. The method of Clause 60, wherein four lenses overlie single ones of the plurality of piezoelectric elements.

62. The method of Clause 55, wherein: the plurality of piezoelectric elements are arranged in an array of rows and columns and are energized by timed amplified driving pulses; and adjacent ones of the plurality of piezoelectric elements are not energized by at least amplified driving pulses chosen from simultaneous driving pulses and temporally sequential driving pulses.

From the foregoing, it will be appreciated that specific embodiments of the present subject matter have been described herein for purposes of illustration, but that various modifications may be made without deviating from the spirit and scope of the present subject matter. Accordingly, the present subject matter is not limited except as by the appended claims.

What is claimed is:

1. A piezoelectric element array assembly, comprising:
a piezoelectric element configured to produce ultrasound energy responsive to amplified driving pulses; and
a lens layer bonded to the piezoelectric element, the lens layer having a plurality of lenses formed therein that are configured to focus ultrasound energy created by the piezoelectric element simultaneously into a corresponding plurality of wells of a microplate disposable in ultrasonic communication with the lens layer.

2. The piezoelectric element array assembly of claim 1, wherein the piezoelectric element includes a column of two piezoelectric elements.

3. The piezoelectric element array assembly of claim 1, wherein the piezoelectric element includes a column of four piezoelectric elements.

4. The piezoelectric element array assembly of claim 1, wherein the piezoelectric element includes a column of six piezoelectric elements.

5. The piezoelectric element array assembly of claim 1, wherein the piezoelectric element includes a column of eight piezoelectric elements.

6. The piezoelectric element array assembly of claim 1, wherein the piezoelectric element includes a column of twelve piezoelectric elements.

7. The piezoelectric element array assembly of claim 1, wherein four lenses overlie the piezoelectric element.

8. The piezoelectric element array assembly of claim 1, wherein the piezoelectric element is made of a material including lead zirconate titanate.

9. The piezoelectric element array assembly of claim 1, wherein the lens layer is made of a material having an acoustic impedance between acoustic impedance of the piezoelectric element and a coupling fluid that is disposable between the lens layer and the microplate.

10. The piezoelectric element array assembly of claim 1, wherein the lens layer is made of a material chosen from graphite and fluorphlogopite mica in a borosilicate glass matrix.

* * * * *